(12) United States Patent
Nishino

(10) Patent No.: US 8,854,788 B2
(45) Date of Patent: Oct. 7, 2014

(54) ION GENERATING APPARATUS AND ION PRESENCE DETERMINING METHOD

(75) Inventor: Masafumi Nishino, Osaka (JP)

(73) Assignee: Sharp Kabushiki Kaisha, Osaka (JP)

( * ) Notice: Subject to any disclaimer, the term of this patent is extended or adjusted under 35 U.S.C. 154(b) by 25 days.

(21) Appl. No.: 13/579,111

(22) PCT Filed: Nov. 2, 2010

(86) PCT No.: PCT/JP2010/069492
§ 371 (c)(1),
(2), (4) Date: Aug. 24, 2012

(87) PCT Pub. No.: WO2011/102026
PCT Pub. Date: Aug. 25, 2011

(65) Prior Publication Data
US 2012/0313005 A1    Dec. 13, 2012

(30) Foreign Application Priority Data
Feb. 19, 2010   (JP) .................................. 2010-034895

(51) Int. Cl.
A61L 9/22       (2006.01)
F24F 3/16       (2006.01)
G01N 27/60      (2006.01)

(52) U.S. Cl.
CPC ................ *F24F 3/16* (2013.01); *G01N 27/605* (2013.01); *A61L 9/22* (2013.01)
USPC .......................................... 361/231; 250/435

(58) Field of Classification Search
USPC ................ 250/432 R, 426, 435, 436; 422/22; 361/231
See application file for complete search history.

(56) References Cited

U.S. PATENT DOCUMENTS

| 2003/0113936 A1 | 6/2003 | Yamamoto |
| 2006/0233660 A1* | 10/2006 | Furuhashi et al. .............. 422/28 |
| 2011/0155922 A1 | 6/2011 | Funabiki et al. |

FOREIGN PATENT DOCUMENTS

| JP | 08-062180 A | 3/1996 |
| JP | 2001-099821 A | 4/2001 |
| JP | 2004-319183 A | 11/2004 |

(Continued)

OTHER PUBLICATIONS

Official Communication issued in International Patent Application No. PCT/JP2010/069492, mailed on Nov. 30, 2010.

(Continued)

*Primary Examiner* — Jack Berman
*Assistant Examiner* — Eliza Osenbaugh-Stewar
(74) *Attorney, Agent, or Firm* — Keating & Bennett, LLP

(57) ABSTRACT

It is expected to provide an ion generating apparatus and an ion presence determination method that can prevent the lower accuracy of the ion presence determination caused by the humidity effect. The ion generators are switched ON at the different timing, the electrical potential of the collecting electrode is measured to determine that the ion is present (or not present) when the voltage difference is larger (or smaller) than the threshold. A humidity detecting unit is arranged in a duct. The set threshold for the determination is based on the humidity of the humidity detecting unit, and the ion presence determination is not performed when the humidity is equal to or more than a predetermined humidity. When the determination representing no ion is obtained predetermined times, the warning is output for the users with a LED of a display, a buzzer of a controller or the like.

19 Claims, 16 Drawing Sheets

(56) References Cited

FOREIGN PATENT DOCUMENTS

| | | | |
|---|---|---|---|
| JP | 2005-327696 A | 11/2005 | |
| JP | 2007-114177 A | 5/2007 | |
| JP | 2007-232728 A | 9/2007 | |
| JP | 2007-287334 A | 11/2007 | |
| JP | 2008-220328 * | 8/2008 | ............. G01R 29/24 |
| JP | 2008-203056 A | 9/2008 | |
| JP | 2009-283305 A | 12/2009 | |
| JP | 4411356 B1 | 2/2010 | |
| JP | 2010-225558 A | 10/2010 | |

OTHER PUBLICATIONS

English translation of the Official Communication issued in corresponding Chinese Patent Application No. 201080064082.6, mailed on Jan. 28, 2014.

* cited by examiner

US 8,854,788 B2

ION GENERATING APPARATUS AND ION PRESENCE DETERMINING METHOD

CROSS-REFERENCE TO RELATED APPLICATION

This application is the national phase under 35 U.S.C. §371 of PCT International Application No. PCT/JP2010/069492 which has an International filing date of Nov. 2, 2010 and designated the United States of America.

BACKGROUND OF THE INVENTION

1. Field of the Invention

The present invention relates to an ion generating apparatus including a function for determining a presence of an ion in the air, and an ion presence determining method.

2. Description of Related Art

Recently, it is well known about a technique utilizing positive (plus) ions and/or negative (minus) ions for cleaning the air in a living space. For example, an ion generating apparatus such as an air cleaner including a function for generating ions is known to contain an ion generator for generating plus and minus ions at the middle of an internal air duct, and emit the generated ions with the air to an external space of the apparatus.

When the ion concentration is about 1000-2000 per $cm^3$ in the space into which the ions are emitted, it is possible to obtain a significant effect to eliminate bacteria, such as *Serratia marcescens* and *Bacillus* bacteria. In addition, the ions in the air not only inactivate airborne particles but also denature odorant components. Thus, the air is cleaned in the entire living space.

A general ion generator providing the effect described above applies a drive voltage, for a high voltage alternating current, at a portion between a needle electrode and a counter electrode, or a portion between a discharge electrode and a dielectric electrode, to generate the corona discharge and then to generate plus and minus ions. It is possible to enhance the ion concentration in the air with the utilization of plural ion generators.

On the other hand, if the discharge electrode is damaged by sputtering ejection due to the corona discharge because the ion generator is operated for a long period or a contaminant such as chemical compound or dust accumulatively attaches to the discharge electrode, the amount of generated ions is decreased. Thus, it is important to determine the presence of ions in the air, for notifying users of the requirement maintaining the ion generator.

For example, Patent Document 1 discloses an ion detecting apparatus and an ion generating apparatus that comprise a collecting electrode to collect ions in the air and detects (determines) the presence of ions based on the electric potential change of the collecting electrode at the beginning of ion generating operation (or at the ending of ion generating operation).

Patent Document 1: Japanese Patent Application Laid-Open No. 2007-114177

SUMMARY OF THE INVENTION

As described above, it is conventionally known that a plus ion $H^+(H_2O)_m$ (m may be any natural number) and a minus ion $O_2^-(H_2O)_n$ (n may be any natural number) react together and then eliminate airborne bacteria and the like. However, these ions disappear because of recombination. Thus, the concentration of these ions is drastically decreased in dependence upon the distance from the ion generator, even when high concentration of these ions is implemented in a space close to the ion generator. Therefore, it is the best for the concentration of these ions to implement 2-3,000 per $cm^3$ in a large space, such as an actual living space and working space, although it will be possible to reach tens of thousands per $cm^3$ in a small space such as an experimental setup.

Present inventors found under the experimental condition that the concentration of these ions 7,000 per $cm^3$ can eliminate 99% of avian influenza virus in 10 minutes, and that the concentration of these ions 50,000 per $cm^3$ can eliminate 99.9% of avian influenza virus in 10 minutes. These elimination rates means that 10 per $cm^3$ of the virus remains with the lower concentration but only 1 per $cm^3$ of the virus remains with the higher concentration if there are previously 1,000 per $cm^3$ of the virus in the air. In other words, it is possible to make the remaining virus 10 times lesser by enhancing the ion concentration from 7,000 per $cm^3$ to 50,000 per $cm^3$.

Therefore, it is considered that the enhancement of ion concentration in the entire living space and working space is important for preventing the infectious disease and cleaning the environment.

However, the technique disclosed by Patent Document 1 may hardly determine the presence of ions, because the amount of electrical change on the collecting electrode becomes smaller when the air to be determined for the concentration and presence of ions has higher temperature and higher humidity. Furthermore, after the ion generator is operated for a longer period, the amount of ions generated by the ion generator becomes smaller. Therefore, it may become further difficult to determine the presence of ions because the amount of electrical change on the collecting electrode becomes even smaller.

The present invention is made in view of such circumstances, and has an object to provide an ion generating apparatus and an ion presence determining method that can prevent the humidity from decreasing the accuracy of determining the presence of ions.

An ion generating apparatus according to the present invention has plural ion generator generating plus ion and minus ions, a driving circuit turning on/off the ion generators, an ion detector detecting a criterion representing a generating condition of ions generated by the ion generator, and a determining means for determining a presence of ions based on the criterion detected by the ion detector, and comprises: a humidity detecting means for detecting a humidity, wherein the determining means is configured to determine that ions are present, when the driving circuit turns on one of ion generators and another of ion generators with cyclically different timings and a difference of criterions detected by the ion detector is more than a predetermined threshold, and the determining means is configured not to determine, when the humidity detected by the humidity detecting means is more than a predetermined humidity.

In addition, an ion generating apparatus according to the present invention further comprises: a threshold setting means for setting the threshold based on the humidity detected by the humidity detecting means.

In addition, an ion generating apparatus according to the present invention is configured to make the threshold setting means set the threshold to be smaller when the humidity detected by the humidity detecting means is higher, and sets the threshold to be larger when the humidity detected by the humidity detecting means is lower.

In addition, an ion generating apparatus according to the present invention further comprises: a warning means for warning when the determining means continuously determines predetermined times that ions are not present.

In addition, an ion presence determining method according to the present invention is for making an ion detector detect a criterion representing ion generating condition caused by plural ion generators that generate plus and minus ions, and determining a presence of ions based on the criterion detected by the ion detector, wherein a humidity is detected, it is determined that the ions are present, when one of ion generators and another of ion generators are turned on with cyclically different timings and a difference of criterions detected by the ion detector is more than a predetermined threshold, and the determining is not performed when the detected humidity is more than a predetermined humidity According to the present invention, it is determined that ions are present (or ions are not present), when plural ion generators generating plus and minus ions are turned on one or more times at the different timings and the difference of criterions representing ion generating conditions is more than (or less than) a predetermined threshold. In the case where plural ion generators are turned on at different timings, the difference in criterions detected when the ion generators are turned on is larger than a change amount of criterions detected when only one ion generators are turned on/off. This facilitates determining the presence of ions.

Further, the ion generating apparatus is provided with the means for detecting humidity. The difference of criterions representing the ion generating condition becomes smaller and makes the determination of ion presence more difficult, when the humidity is higher. Thus, it is configured that no determination of ion presence is performed (or no detection of ions is performed) when the detected humidity is more than a predetermined humidity.

Therefore, it is possible to avoid the ion presence determination having a low accuracy.

According to the present invention, the threshold compared with the difference in criterions is set on the basis of the detected humidity, because the environmental humidity causes to change the amount of ions generated by the ion generator, and the detection accuracy of the ion detector. For example, when the difference of criterions detected by the ion detector is decreased at a high humidity environment, the threshold for the higher detected humidity is set to be smaller and the threshold for the lower detected humidity is set to be larger.

Therefore, it is possible to perform accurate determination of ion presence even at the high humidity environment.

According to the present invention, it is additionally configured to warn the user when the determination continuously shows predetermined times that no ions are present. Therefore, it is possible to notify the user that the amount of generated ions is decreased, to urge the user to maintain the ion generator, i.e., clean or change the ion generator.

In the present invention, it is configured to perform the determination of ion presence based on the difference of criterions detected by the ion detector only at the environment whose humidity is less than a predetermined humidity, but not at the high humidity environment whose humidity is more than the predetermined humidity. In other words, the ion presence is not determined at the high humidity environment that tends to make the amount of ions generated by the ion generator and the detection accuracy of the ion detector become unstable. Thus, it is possible to prevent the reduction in the determination accuracy of the ion presence caused by the humidity. Therefore, it is possible to prevent the ion generating apparatus from performing an operation based on the determination result of ion presence having the low accuracy, for example, when the amount of generated ions is decreased, the accuracy of the ion detector is decreased or the like at the high humidity environment.

The above and further objects and features of the invention will more fully be apparent from the following detailed description with accompanying drawings.

DESCRIPTION OF THE PREFERRED EMBODIMENTS

Figure 1:
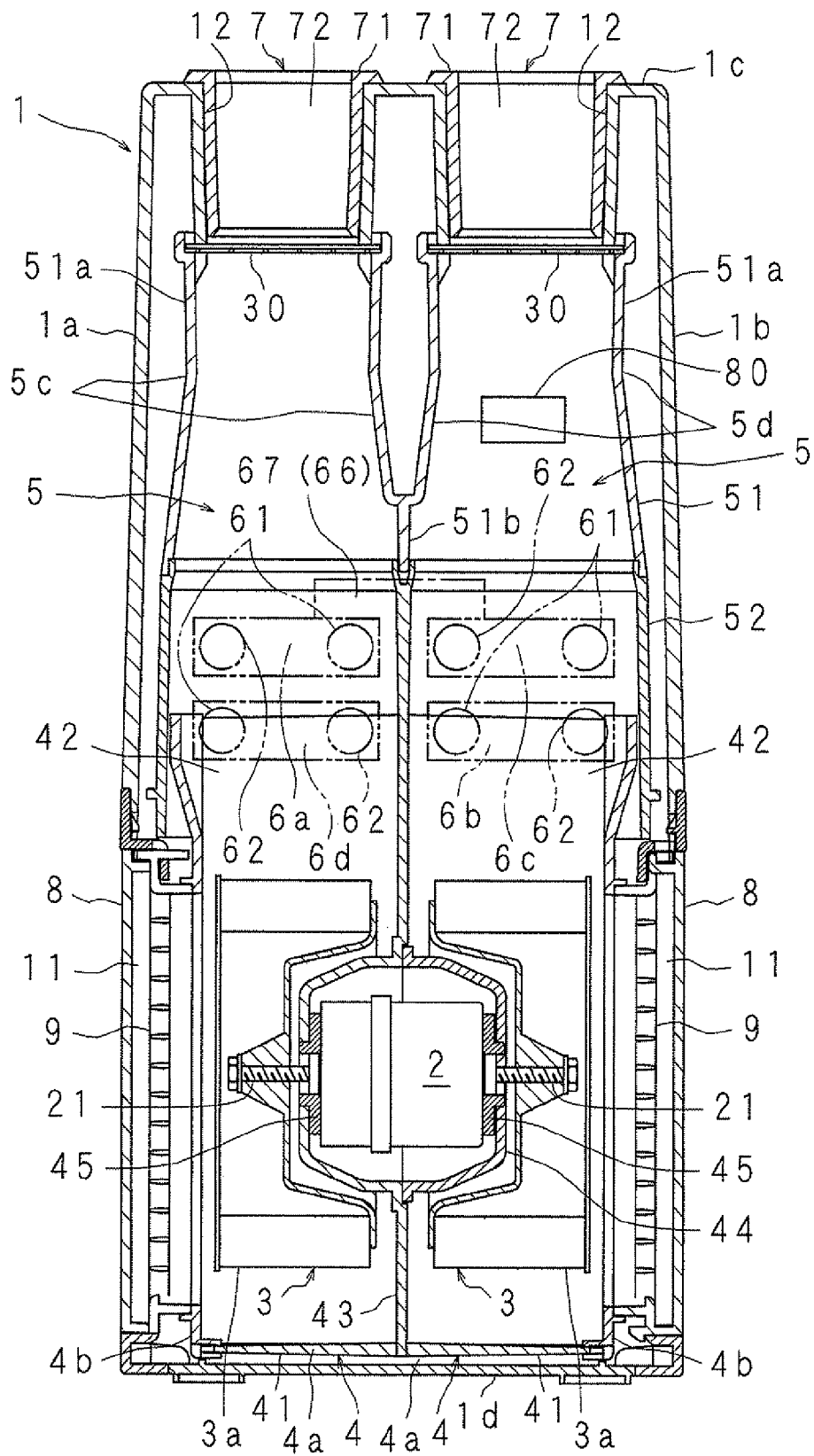
FIG. 1 is a front cross section view that shows a configuration of an ion generating apparatus according to the present invention.
Figure 2:
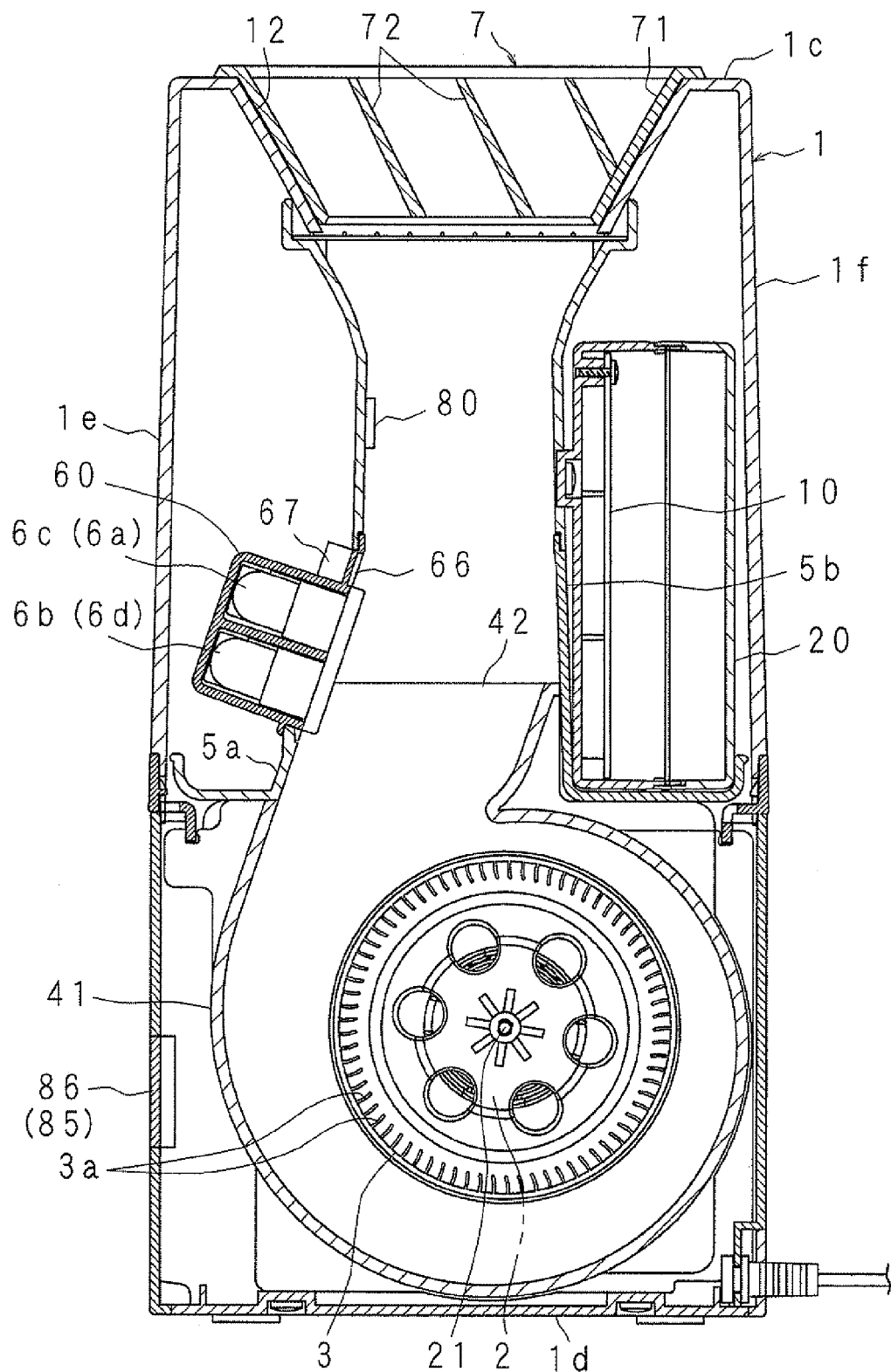
FIG. 2 is a side cross section view that shows the configuration of the ion generating apparatus.
Figure 3:
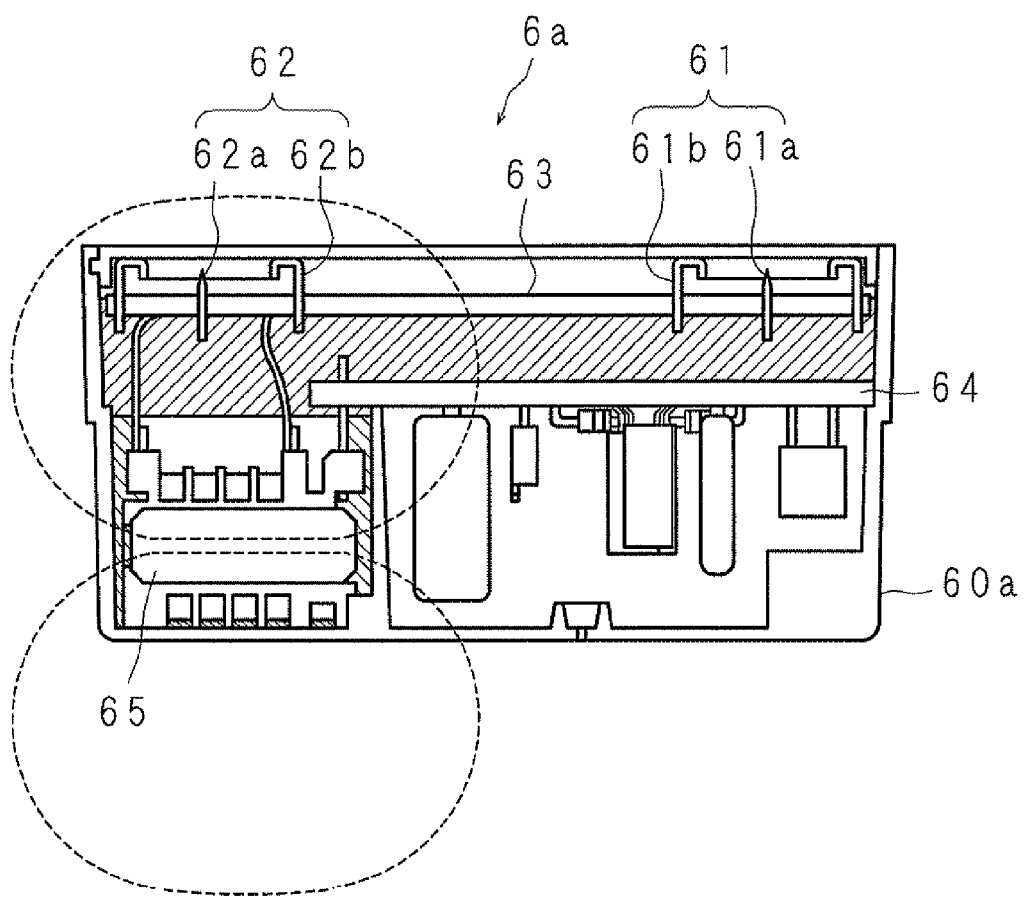
FIG. 3 is a front cross section view showing a configuration of an ion generator.
Figure 4:
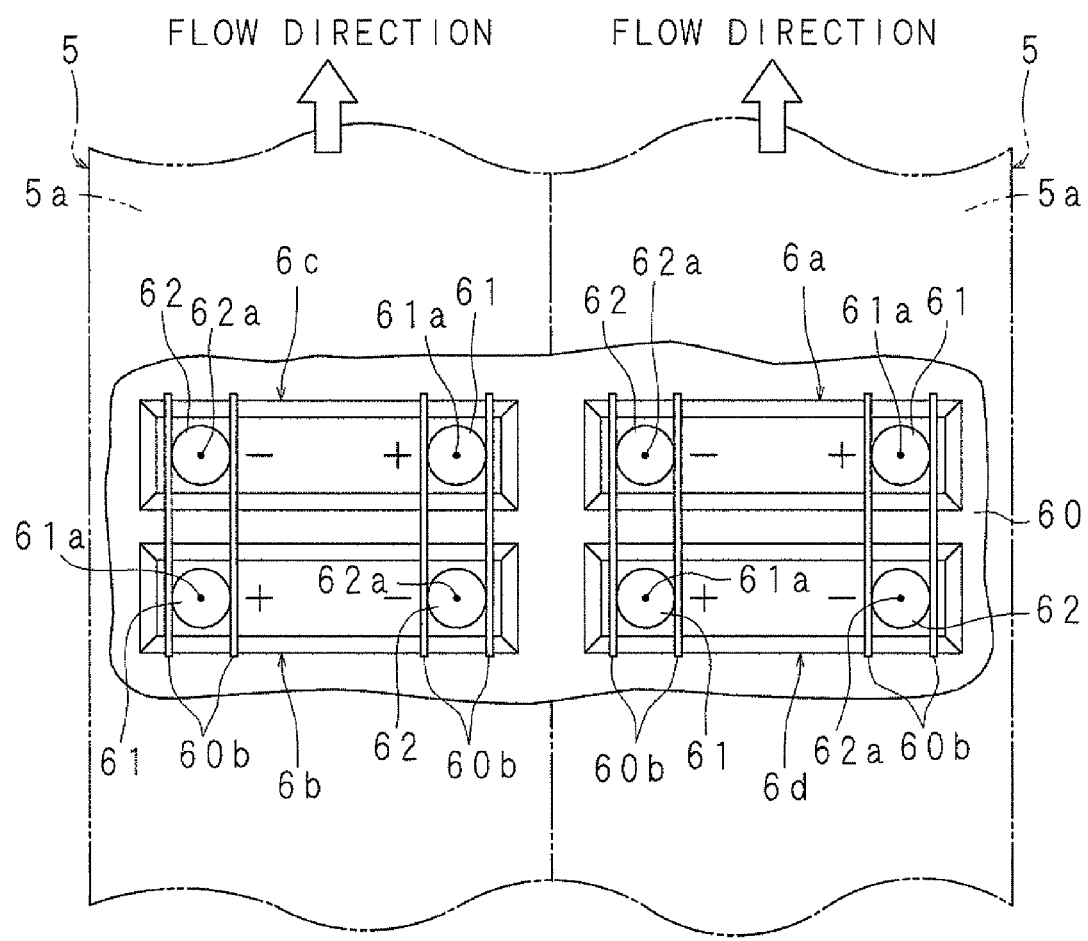
FIG. 4 is an elevation view that schematically shows ion generators attached to a front wall and viewed from the inside of a housing.

Hereinafter, an embodiment of the present invention is described in detail with reference to the figures. FIG. 1 is a front cross section view that shows a configuration of an ion generating apparatus according to the present invention. FIG. 2 is a side cross section view that shows the configuration of the ion generating apparatus. FIG. 3 is a front cross section view showing a configuration of an ion generator 6a. Configurations of the other generators 6b, 6c 6d are similar to the ion generator 6a, and omitted in FIG. 3. In addition, FIG. 4 is an elevation view that schematically shows the ion generators 6a, 6b, 6c, 6d attached to a front wall 5a and viewed from the inside of a housing 1.

A reference numeral "1" in figures represents the housing of the ion generating apparatus. The housing 1 is substantially formed in a rectangular parallelepiped shape, and includes side walls 1a, 1b respectively provided with inlet ports 11, 11 at the bottom and opposed with a distance to each other, and a top wall 1c provided with two fitting holes 12, 12 at the center. A motor 2 is arranged at the bottom in the housing 1 to have output axes 21, 21 at the both sides in the rotating direction. The output axes 21, 21 of the motor 2 are respectively provided with two bladed wheels 3, 3, contained in two casings 4, 4, which are rotatable. A combination of the motor 2, bladed wheels 3, 3 and casings 4, 4 configures a fan.

Two ducts 5, 5 are arranged as cylinders above the bladed wheels 3, 3, to pass upwardly the air generated by the rotations of bladed wheels 3, 3. Two of ion generators 6a, 6b, 6c, 6d are arranged at the bottom of each duct 5, 5, as one of two is arranged at the top and the other one of two is arranged at the bottom. Each of ion generators 6a, 6b, 6c, 6d includes two ion generating units 61, 62. A collecting electrode 66 and a measuring unit 67 are arranged above the ion generators 6a, 6c that are arranged at the top side. The shape of the collecting electrode 66 viewed from the front side is substantially rectangle, and the collecting electrode 66 is configured to collect generated ions. The measuring unit 67 is configured to measure the electric potential of the collecting electrode 66. The collecting electrode 66 and the measuring unit 67 are adjacent to the ion generators 6a, 6c, and the longitudinal directions of them are kept horizontally. Each of ducts 5, 5 includes a wind guide 7, 7 that is detachably arranged at the fitting hole 12, 12.

The housing 1 further includes a bottom wall 1d, a front wall 1e and a back wall 1f. The shape of the bottom wall 1d viewed from the front side is a rectangle. The front wall 1e and the back wall 1f are continuous to front and back sides of the bottom wall 1d. A controller 85 and a display 86 are arranged at the bottom of front wall 1e. The controller 85 is configured to accept an instruction for the ion generating apparatus. The display 86 consists of a LED showing information, such as warning and operation condition. Filters 8, 8 are provided with the inlet ports 11, 11 arranged at the bottom of side walls 1a, 1b. The filters 8, 8 are utilized for passing the air flown into the inlet ports 11, 11 by the bladed wheels 3, 3 and for removing the contaminant in the passing air to clear the air. The shape of each fitting hole 12, 12 viewed from the front side is substantially rectangle whose longitudinal direction is kept to the front and back direction, as the fitting holes 12, 12 are arranged on the top wall 1. The inner surface at the front side of each fitting hole 12, 12 is inclined frontward with respect to the vertical direction, and the inner surface at the back side of each fitting hole 12, 12 is inclined backward with respect to the vertical direction. The housing 1 can be divided into a top portion and a bottom portion at the middle in the top and bottom direction. A casing 4, 4 is attached to the bottom portion, and a duct 5, 5 is attached to the top portion.

Each bladed wheel 3, 3 is a multi-blade fan including plural blades 3a whose rotation center side with respect to the outer edge will change in the rotation direction. In other words, each bladed wheel 3, 3 is a sirocco fan formed in a cylindrical shape. In addition, each bladed wheel 3, 3 includes an axle bearing plate at the end. An output axis 21, 21 of the motor 2 is attached to an axial hole opened at the center of the axel bearing plate. Thus, each bladed wheel 3, 3 is configured to release, from a peripheral portion between blades 3a, of the air flown into the center of air hole from the opening at the other end.

Each casing 4, 4 includes a circular guide wall 41, 41 and an outlet port 42, 42. The circular guide wall 41, 41 is configured to guide the air, generated by the rotation of bladed wheel 3, 3, toward the rotational direction of the bladed wheel 3, 3, to enhance the speed of air. The outlet port 42, 42 is upwardly opened from a part of the circular guide wall 41, 41 to one side of tangential direction for the circular guide wall 41, 41. The outlet port 42, 42 is formed in a rectangular cylinder shape protruding from a part of the circular guide wall 41, 41 to one side of the tangential direction for the circular guide wall 41, 41, with an inclined angle with respect to the vertical direction.

Each casing 4, 4 is formed in a dish shape and includes a casing main body 4a, 4a and a cover 4b, 4b. The casing main body 4a, 4a includes the circular guide wall 41, 41 and an opening portion for the outlet port 42, 42. The cover 4b, 4b covers the opening side of casing main body 4a, 4a, and has an opened portion that corresponds to the opening of the bladed wheel 3, 3. Opposing sides of casing main bodies 4a, 4a are integrally joined by a join wall 43 for partitioning. In addition, a vent plate 9, 9 are arranged between the opening portion of the cover 4b, 4b and the filter 8, 8, as including plural vent holes.

A portion of the join wall 43 corresponding to the motor 2 includes a recess that is secluded to one casing main body 4a side. A dish shape supporting plate 44 is attached to the edge of recess. The motor 2 is sandwiched and supported through rubber plates 45, 45 between the recess and the supporting plate 44. The output axis 21, 21 is inserted into the axial hole provided at the center of recess and supporting plate 44. The bladed wheel 3, 3 is attached to the output axis 21, 21. In addition, the top end of join wall 43 is extending upward from the casing 4, 4.

The bottom end of duct 5, 5 is continuous to the outlet port 42, 42 and the top end of duct 5, 5 is continuous to the fitting hole 12, 12. Then, the duct 5, 5 is formed in a rectangular cylinder shape whose middle portion in the top and bottom direction is narrow. In addition, the duct 5, 5 includes front walls 5a, 5a (only one of them is shown in FIG. 2) arranged along one of tangential directions of circular guide walls 41, 41 from the outlet ports 42, 42, and includes back walls 5b, 5b (only one of them is shown in FIG. 2) arranged vertically from the outlet ports 42, 42. A front wall 5a, 5a and a back wall 5b, 5b are respectively continue to two side walls 5c, 5c, 5d, 5d that are vertically arranged. Thus, the air coming from the outlet ports 42, 42 flows vertically as the laminar air flow along the front walls 5a, 5a, the back walls 5b, 5b and the side walls 5c, 5c, 5d, 5d.

The front walls 5a, 5a includes a through hole for corresponding to a support 60 that supports the ion generator 6a, 6b, 6c, 6d, the collecting electrode 66 and the measuring unit 67. The support 60 is fit into the through hole for the attachment. A circuit board 10 and a cover 20 are attached to the back wall 5b, 5b. The circuit board 10 is connected to the motor 2, the ion generators 6a, 6b, 6c, 6d, the measuring unit 67 and the power line. The cover 20 covers the circuit board 10.

A humidity detector 80 is arranged on the front wall 5a of one duct 5, to detect the humidity in the duct 5. The humidity detector 80 is a polymer resistance type humidity sensor, and utilizes the change of electrical characteristics (resistance values) based on the water absorbance and release of the polymer membrane, to detect the humidity. It should be noted that the humidity detector 80 is not limited to the polymer resistance type humidity sensor. It is possible as the humidity detector 80 to utilize a polymer based capacitive humidity sensor, a metal oxide humidity sensor with ceramic, an electrolytic humidity sensor with lithium chloride, or the like. The humidity detector 80 is electrically connected to the circuit board 10.

The duct 5, 5 is divided into a duct top portion 51 and a duct bottom portion 52, at the middle in the vertical direction. The duct bottom portion 52 is formed in a polygonal cylinder shape, and separated at the center in the horizontal direction by the join wall 43. The duct top portion 51 includes a part under the polygonal cylinders 51a, 51a aligned with a space in the horizontal direction, the part is integrally continued to a connection portion 51b, and the duct top portion 51 is separated by the connecting portion 51b and the join wall 43. Guard nets 30, 30 are arranged on the top end of the duct top portion 51, to guard from the insertion of a foreign substance, such as a finger.

The wind guide 7, 7 includes a polygonal rim portion 71, 71 and plural wind direction plates 72, 72 and is formed in a similar shape. A cross-sectional shape of the polygonal rim portion 71, 71 in the front and back direction is a trapezoid whose top side is longer than the bottom side. The plural direction plates 72, 72 are aligned with a space in the front and back direction within the polygonal rim portion 71, 71, and inclined with respect to the vertical direction toward one of the front and back directions. The front and back walls of the polygonal rim portion 71, 71 are inclined with respect to the vertical direction toward the front and back direction.

Each of the ion generators 6a, 6b, 6c, 6d is arranged in a case 60a whose shape is a substantially parallelepiped, and includes two ion generating units 61, 62 aligned with a space in a direction perpendicular to a flow direction of the air generated by the rotating bladed wheels 3, 3. The ion generating units 61, 62 are arranged on the electrode board 63, and include sharp discharge electrodes 61a, 62a and induction electrodes 61b, 62b surrounding the discharge electrodes 61, 62a, respectively. When high voltage is applied, the discharge electrodes 61, 62 generate the corona discharge, respectively. Thus, one ion generating unit 61 generates plus ions and another ion generating unit 62 generates minus ions to the opening side of respective dielectric electrodes 61b, 62b.

The electrode board 63 is arranged opposite to the circuit board 64 including circuit elements, such as a transistor, resistance and the like. The circuit board 64 includes a booster transformer 65 at a side opposing to the generating unit 62 of the minus ion. The booster transformer 65 is for generating the high voltage. The winding direction of the winding wire of the booster transformer 65 is configured to make the magnetic flux leaked from the winding wire become substantially parallel to the alignment direction of the ion generating units 61, 62 at the vicinity of the ion generating unit 62 (shown by the broken line in FIG. 3). Synthetic resin is filled between the electrode board 63 and the circuit board 64, and around the booster transformer 65.

The ion generators 6a, 6b, 6c, 6d are supported by the support 60 and attached to the front walls 5a, 5a of the ducts 5, 5, respectively. The alignment direction of the ion generating units 61, 62 is the same for the ion generator 6a, 6c and the ion generator 6b, 6d that are arranged in parallel to the alignment direction and perpendicular to the flow direction. The alignment direction of ion generating units 61, 62 for the ion generator 6a, 6c is opposite to the alignment direction of ion generator 6b, 6d, and the ion generator 6a, 6c and the ion generator 6b, 6d are arranged in the flow direction. Each ion generating unit 61, 62 for the ion generator 6a, 6b, 6c, 6d is directed from the though hole to the inside of duct 5, 5. Ribs 60b, 60b are arranged at the both ends of ion generating units 61, 62 arranged in the flow direction. The ribs 60b, 60b are for preventing users from directly touching the discharge electrodes 61a, 62a.

The collecting electrode 66 is configured with a rectangular flat electrode collecting ions. The collecting electrode 66 is arranged near the ion generating units 62, 61 and the electrode surface is exposed inside the duct 5, 5, for intensively detecting the minus and plus ions respectively generated by the ion generating unit 62 of the ion generator 6a and the ion generating unit 61 of the ion generator 6c. The electrode surface of the collecting electrode 66 is substantially parallel to the arranged direction of the ion generators 6a, 6c. When the collecting electrode 66 collects a plus ion (or minus ion), the electrical potential of the collecting electrode 66 is increased (or decreased). The measuring unit 67 described later measures the electrical potential of the collecting electrode 66 as the voltage value with respect to the electrical potential of ground.

Although it is illustrated that the collecting electrode 66 is arranged near the ion generating unit 62 of the ion generator 6a and the ion generating unit 61 of the ion generator 6c, the present invention is not limited to the illustration. For example, the collecting electrode 66 may be arranged at a proper site in the fitting hole 12, or at a proper site on the side walls 1a, 1b, top wall 1c, front wall 1e, or back wall 1f of the housing 1.

The ion generating apparatus configured as described above is kept in a room. When the motor 2 of the fan is driven, the bladed wheels 3, 3 rotate to take the room air into two casings 4, 4 from the inlet ports 11, 11 arranged at the both sides. The contaminant, such as a dust, is removed from the intake room air by the filters 8, 8. At that time, the air taken into the casings 4, 4 becomes the laminar air flow because of the circular guide walls 42, 42 around the bladed wheels 3, 3. The laminar air flow comes to the outlet ports 42, 43 along the circular guide walls 41, 41, and comes out from the outlet ports 42, 42 into the ducts 5, 5.

Figure 5:
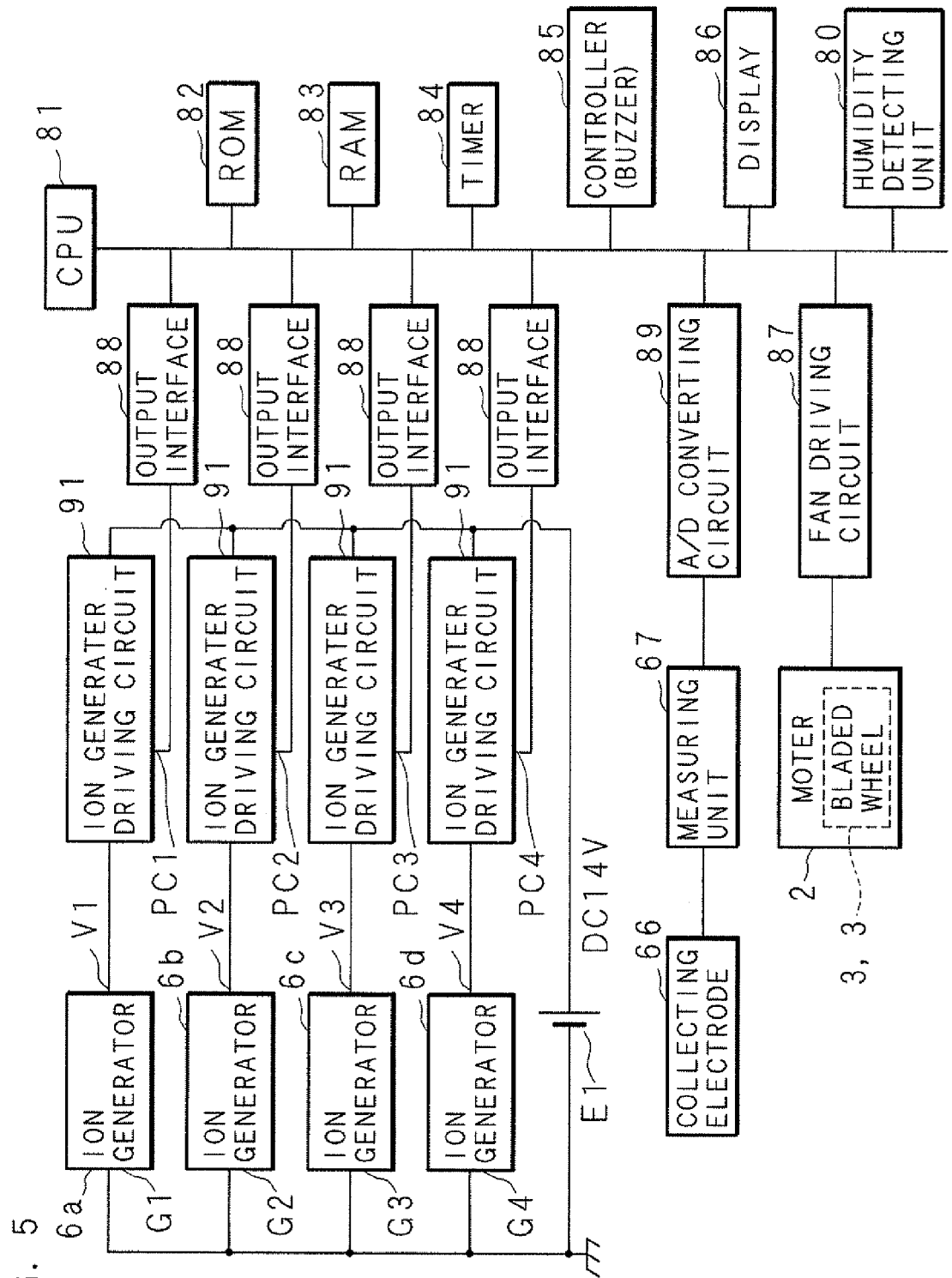
FIG. 5 is a block diagram that shows a schematic configuration of a control system in the ion generating apparatus.

FIG. 5 is a block diagram that shows a schematic configuration of a control system in the ion generating apparatus. A CPU 81 works as the center of the control system, and is connected to a ROM 82, a RAM 83 and a timer 84 with the bus connection style. The ROM 82 is for storing information, such as programs. The RAM 83 is for storing information that is generated temporarily. The timer 84 is for measuring time. The CPU 81 performs processing, such as an input, an output, and a calculation, based on control programs that have been stored previously in the ROM 82.

The CPU 81 is further connected to a controller 85, a display (warning means) 86, a fan driving circuit 87, an A/D converting circuit 89, and a humidity detecting unit 80, with the bus connection style. The controller 85 is for accepting an instruction to change the air volume of the ion generating apparatus. The display 86 is configured with LEDs that shows information, such as warning and operating condition. The fan driving circuit 87 is for driving the motor 2 attached to the bladed wheels 3, 3. The A/D converting circuit 89 is for converting an analog voltage measured by the measuring unit 67 into a digital voltage and then obtaining the digital voltage, as the measuring unit 67 is for measuring the electrical potential of the collecting electrode 66. The controller 85 includes a buzzer (warning means) for outputting the warning sound. The collecting electrode 66 and the measuring unit 67 configure the ion detector.

Each output terminal of output interfaces 88, 88, 88, 88 connected to the CPU 81 with the bus connection style is connected to a control input PC1, PC2, PC3, PC4 of an ion generator driving circuit 91, 91, 91, 91 which has two output terminals. One output terminal of each ion generator driving circuit 91, 91, 91, 91 is connected to an anode of a 14V DC power source E1, and the other output terminal is connected to each power input V1, V2, V3, V4 of ion generators 6a, 6b, 6c, 6d. Each grounded input G1, G2, G3, G4 of ion generators 6a, 6b, 6c, 6d and an cathode of the DC power source E1 are connected to the electrical potential of ground.

Every time the timer 84 measures a predetermined time period in the case that the ion generating apparatus is normally operating, the CPU 81 reverses (changes) the ON/OFF of the control inputs PC1, PC2, PC3, PC4 of the ion generator driving circuits 91, 91, 91, 91, through the output interfaces 88, 88, 88, 88. Thus, each of the ion generator driving circuits 91, 91, 91, 91 connects/disconnects the power inputs V1, V2, V3, V4 of the ion generators 6a, 6b, 6c, 6d and the anode of the DC power source E1, at each predetermined time period.

Figure 6:
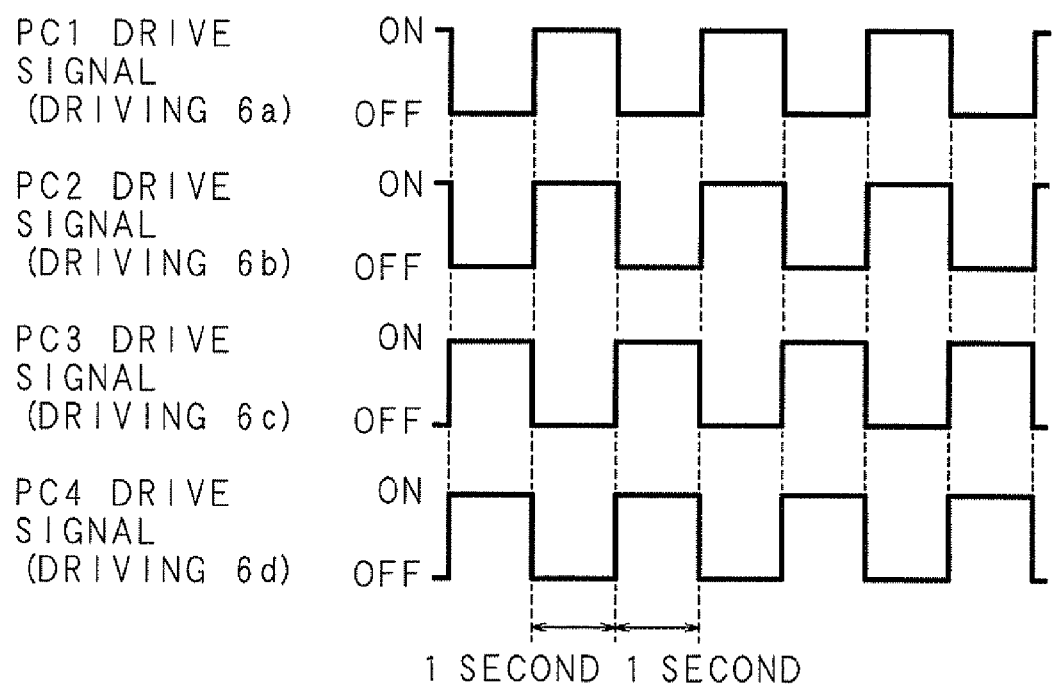
FIG. 6 is a timing chart that shows drive signals input into a control input when the ion generating apparatus is in a normal operable condition.

FIG. 6 is a timing chart that shows drive signals input into the control input PC1, PC2, PC3, PC4 when the ion generating apparatus is in a normal operable condition. The horizontal axis represents time (second) and the vertical axis represents the ON/OFF condition in the figure. The drive signal input into the control input PC1, PC3 repeats alternately ON for one second and OFF for one second, with 50% duty cycle. The drive signal input into the control input PC1, PC2 and the control input PC3, PC4 are configured to repeat the ON/OFF in the same phase. Thus, each of the ion generator driving circuits 91, 91, 91, 91 alternately supplies/not supplies the power to the ion generators 6a, 6b and the ion generators 6c, 6d every other second. Therefore, it is configured to alternately drive the ion generator 6a, 6b and the ion generator 6c, 6d every one second.

Figure 7:
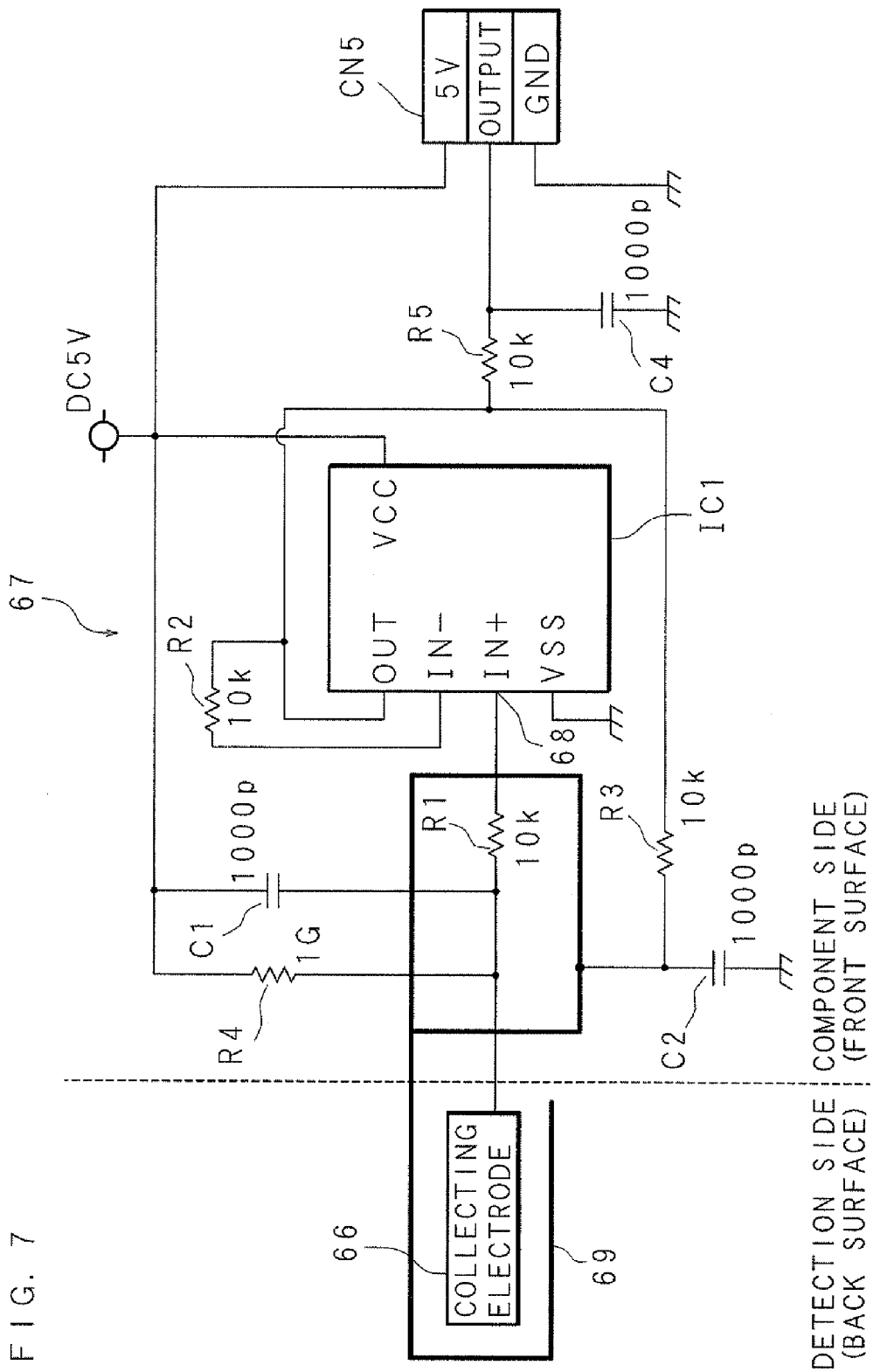
FIG. 7 is a circuit diagram that shows a configuration of an ion detector.

FIG. 7 is a circuit diagram that shows a configuration of the ion detector. The ion detector includes the measuring unit 67 at the component side of the circuit board (front surface) and the collecting electrode 66 at the detection side of the circuit board (back surface).

The measuring unit 67 includes a resistance R4 that pulls the collecting electrode 66 up to the 5V DC power source. Both terminals of the resistance R4 are connected in parallel to a capacitor C1. The collecting electrode 66 is connected to a non-inverting input terminal (IN+) 68 of an operational amplifier IC1, through a protective resistance R1 of the measuring unit 67.

A resistance R2 is connected between the inverting input terminal (IN−) and the output terminal (OUT) of the operational amplifier IC1. The output terminal of the operational amplifier IC1 is connected to a resistance R3 and a resistance R5. The resistance R3 is serially connected to a capacitor C2 that is connected to the electrical potential of ground. The resistance R3 is serially connected to a capacitor C4 that is similarly connected to the electrical potential of ground. A connection point of the capacitor C2 and the resistance R3 is connected to a protective electrode 69. A connection point of the capacitor C4 and the resistance R5 is connected to an output terminal of a connector CN5. The connector CN5 is for giving the electrical potential measured by the measuring unit 67 to the A/D converting circuit 89. The protective electrode 69 is configured to partially surround the collecting electrode 66. In addition, the protective electrode 69 is configured to surround the protective resistance R1 and a portion connected to the both terminals of the protective resistance R1.

When the collecting electrode 66 collects a plus (or minus) ion with the circuit described above, a positive charge of the plus ion (or negative charge of the minus ion) flows into a ground potential side electrode of the capacitor C1 connected to the collecting electrode 66. Thus, the electrical potential at the connection point of the capacitor C1 and the protective resistance R1 is increased (or decreased), and then given to the non-inverting input terminal 68 of the operational amplifier IC1 through the protective resistance R1. On the other hand, the output terminal of the operational amplifier IC1 is returned to the inverting input terminal to make an impedance converter having an amplification degree 1. The electrical potential of this output terminal is the same as the electrical potential given to the non-inverting input terminal 68. This electrical potential is utilized as the analog voltage value with respect to the electrical potential of ground, and output from an output terminal of the connector CN5 through the resistance R5.

An output impedance of the operational amplifier IC1 is significantly smaller than a resistance value of the resistance R3. The protective electrode 69 is configured through the resistance R3 to keep the electrical potential that is the same as the electrical potential of the collecting electrode 66, as the resistance value of the resistance R3 (10 kΩ) is a hundred thousandth of the resistance R4 (1 GΩ) that pulls up the collecting electrode 66. Thus, it is possible to prevent the charge of the ion collected by the collecting electrode 66 from being conducted through the surface of the circuit board and then moving to the outside of the surrounding formed by the protective electrode 69 between the collecting electrode 66 and the operational amplifier IC1.

It should be noted that the protective resistance R1 is not limited to a resistance. For example, it is possible to utilize a series-parallel circuit with circuit components, such as a resistance and a coil, for the purpose other than the protection.

Figure 8A:
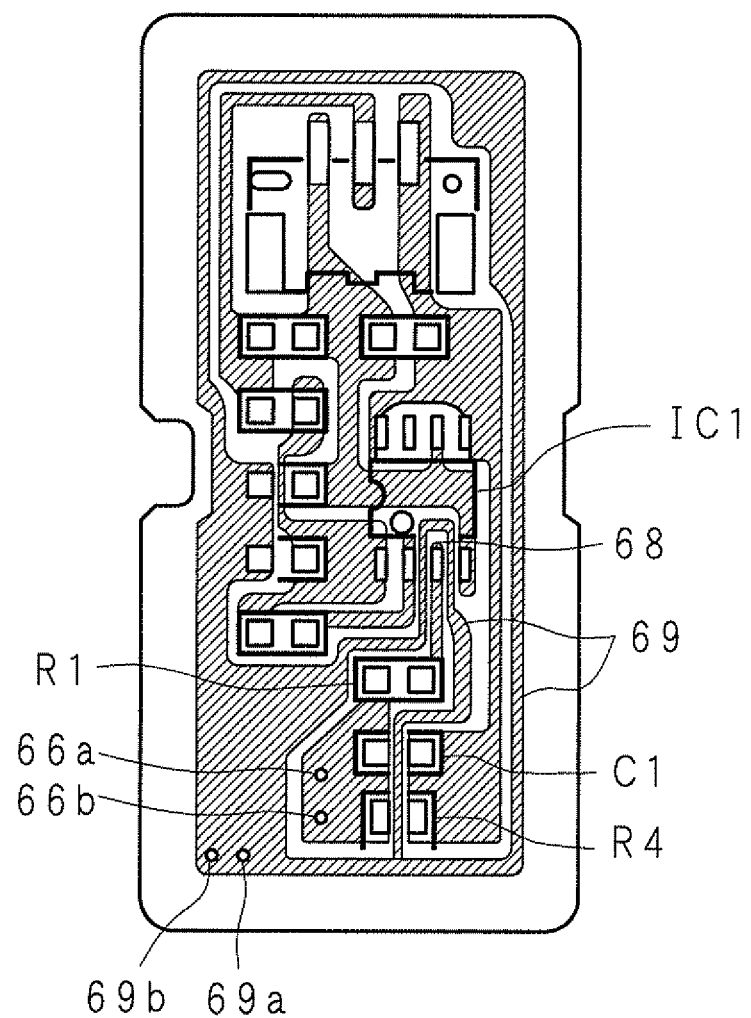
FIG. 8A is a plain view that shows a conductive pattern on a circuit board of the ion detector.
Figure 8B:
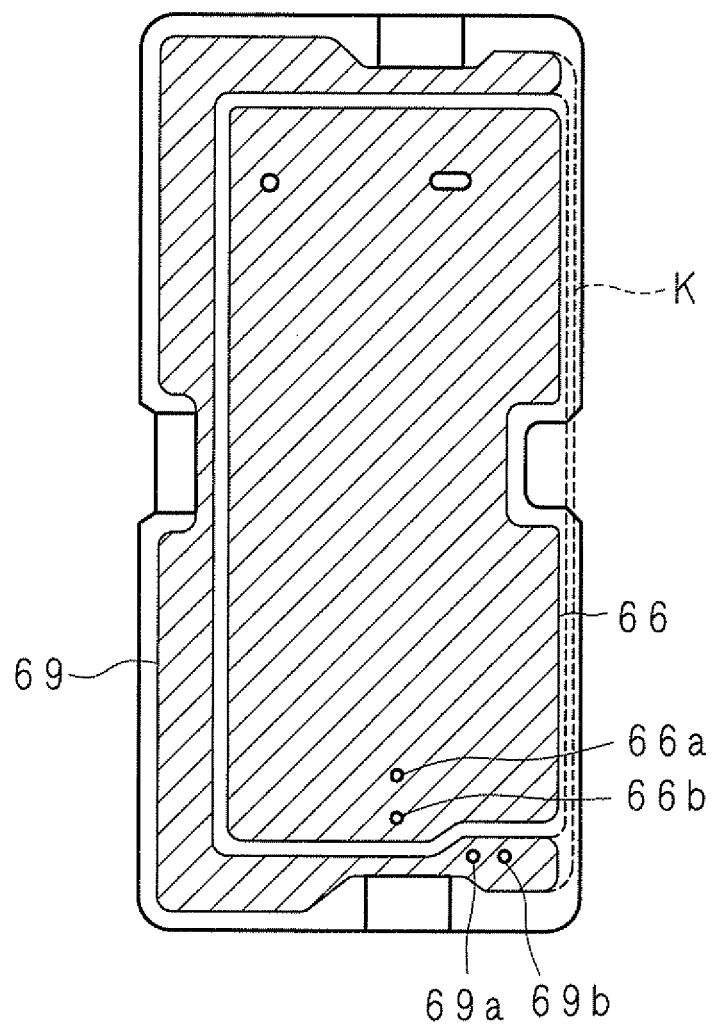
FIG. 8B is a plain view that shows a conductive pattern on a circuit board of the ion detector.

FIG. 8A and FIG. 8B are plain views that show conductive patterns on a circuit board of the ion detector. FIG. 8A shows a conductive pattern on the front surface where circuit components are mounted, and FIG. 8B shows a conductive pattern on the back surface where the collecting electrode 66 and the protective electrode 69 are formed. The collecting electrode 66 is electrically connected to the conductive pattern on the front surface through the through holes 66a, 66b, and this conductive pattern is attached to one of terminals of the protective resistance R1, one of terminals of the resistance R4 and one of terminals of the capacitor C1.

As surrounding the collecting electrode 66 on the back surface, the protective electrode 69 has a plain view formed in a substantial U-shape in which one side in the longitudinal direction of the rectangular circuit board is cut as a deleted portion K. The protective electrode 69 is electrically connected through the through holes 69a, 69a to the protective electrode 69 surrounding the circuit components mounted on the front surface. In addition, the protective electrode 69 on the front surface surrounds this conductive and another conductive pattern connected to the protective resistance R1 and the non-inverting input terminal 68.

A surface of the protective electrode 69 surrounding the conductive pattern described above and the protective resistance R1 is substantially parallel to the surface of the collecting electrode 66. Thus, it is possible to minimize the magnetic flux leaked from the booster transformer 65 and crossed to the protective electrode 69.

Now, it is explained about the minus ion generated by the ion generators 6a, 6b, 6c, 6d. The collecting electrode 66 of the measuring unit 67 mainly collects the minus ions generated by the minus ion generating unit 62 of the ion generator 6a. When ions are not generated, the output voltage of the measuring unit 67 is about 5 V because of the pull-up performed by the resistance R1. When the ion generators 6a, 6b are operated, minus ions are collected by the collecting electrode 66. Thus, the output voltage of the measuring unit 67 is gradually decreased and saturated at a steady voltage value. For example, when the ion generators 6a, 6b are operated in the experimental condition of the inventors of this application, the output voltage is decreased by 1 V and then saturated after nine seconds or more since the operation is started. However, this experimental result is obtained under normal room temperature and normal room humidity. It is known that the output voltage of the measuring unit 67 is not significantly decreased from 5V under high humidity condition.

Then, the inventors of this application focus attention on the difference in output voltages of the measuring unit 67 when ON/OFF of the ion generators 6a, 6c arranged parallel to the alignment direction of ion generating units 61, 62 is switched alternately and then the collecting electrode 66 collects the plus/minus ions alternately. The inventors found that the change amount of the output voltage of the measuring unit 67 tends to be increased by making the ion generators 6a, 6c switch ON/OFF alternately (i.e., the difference with alternate ON situation of ion generators tends to be increased), in accordance with the increase of electrical discharge number, even under the condition that little change of the output voltage of the measuring unit 67 is observed by making the ion generators 6a, 6b switch ON/OFF simultaneously.

When the ion generator 6a, 6b and the ion generator 6c, 6d are alternately switched ON/OFF, the collecting electrode 66 of the measuring unit 67 mainly performs alternate collection of the minus ion generated by the minus ion generating unit 62 of the ion generator 6a and the plus ion generated by the plus ion generating unit 61 of the ion generator 6c. It is found that the waveform of output voltage of the measuring unit 67 can be changed significantly from +5V to the electrical potential of ground, approximately, when the ion generator 6a, 6b and the ion generator 6c, 6d are alternately switched ON/OFF under normal room temperature and normal room humidity.

The output voltage of the measuring unit 6 is not sufficiently decreased from +5V under the high humidity condition, as described above. However, it is found from the experiment of the inventors of this application that the output voltage of the measuring unit 67 is once rapidly decreased immediately after the ion generator 6a, 6b is switched ON in the case that the ion generator 6a, 6b and the ion generator 6c, 6d are alternately switched ON/OFF even under the high humidity condition. Thus, it is possible to determine the presence of ions even under the high humidity condition, by detecting the rapid decrease of the output voltage. Therefore, it is possible to determine the presence of ions, when the ion generator 6a, 6b and the ion generator 6c, 6d are alternately switched ON/OFF at the short interval (e.g., 1 second), the output voltage of the measuring unit 67 immediately before the ion generator 6a, 6b is switched ON is utilized as the base voltage and the change amount to the local minimal value of the output voltage of the measuring unit 67 immediately after the ion generator 6a, 6b is switched ON is referred for the determination.

Figure 9:
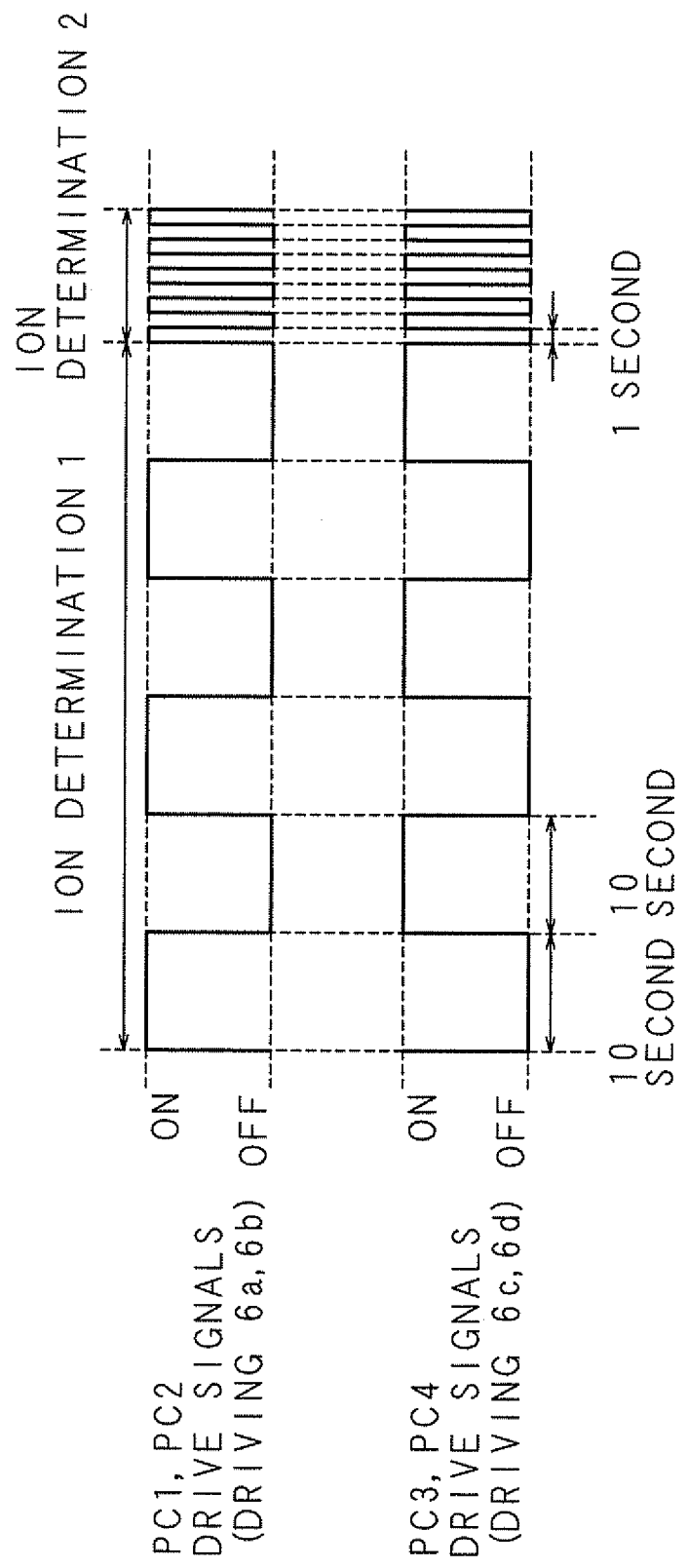
FIG. 9 is a timing chart that shows drive signals input into the control input when the determination of ion presence is performed.

FIG. 9 is a timing chart that shows drive signals input into the control input PC1, PC2, PC3, PC4 when the determination of ion presence is performed. The horizontal axis represents time (second) and the vertical axis represents the ON/OFF condition of drive signals in the figure. The ion generating apparatus according to the embodiment utilizes two methods, i.e., an ion determination 1 and an ion determination 2, for determining the presence of ions. The ion determination 1 is utilized for the determination under normal room temperature and normal room humidity. The ion generator 6a, 6b and the ion generator 6c, 6d are alternately switched ON/OFF every 10 seconds, and then it is determined that the ion is present when the change amount of the output voltage of the measuring unit 67 measured immediately before the ON/OFF is changed is larger than the threshold. The ion determination 2 is utilized for the determination under high humidity condition. The ion generator 6a, 6b and the ion generator 6c, 6d are alternately switched ON/OFF every 1 second, the output voltage of the measuring unit 67 immediately before the ion generator 6a, 6b is switched ON is utilized as the base voltage and then it is determined that the ion is present when the change amount to the local minimal value of the output voltage of the measuring unit 67 immediately after the ion generator 6a, 6b is switched ON is larger than the threshold.

It should be noted that the switch interval of the ion determination 1 is not limited to the 10 seconds and the switch interval of the ion determination 2 is not limited to the 1 second. Their intervals may be longer or shorter.

With the ion determination 1, the ON/OFF of each drive signal is changed 6 times at 10 second interval. When it is determined that the ion is present, the determination of ion presence is normally terminated. When it is not determined that the ion is present, the ion determination 1 is changed to the ion determination 2 and the ON/OFF of each drive signal is changed 10 times at 1 second interval. When it is determined that the ion is present, the determination of ion presence is normally terminated. When it is determined not only with the ion determination 1 but also the ion determination 2 that the ion is not present, it is concluded that the ion is not present and then a predetermined count value is counted up. The ion generating apparatus is configured to repeat such a determination every 3 hours, and to warn when the count value reaches to a predetermined value.

At each interval of the ion determination 1, the drive signals input into the control inputs PC1, PC2 are firstly ON and the drive signals input into the control inputs PC3, PC4 are OFF, and then the ON/OFF of these drive signals are changed after 10 seconds. Further 10 seconds later, one interval is terminated. Thus, only the ion generator 6a, 6b is switched ON during the first 10 seconds, and the minus charges of the minus ions generated by each ion generating unit 62 are accumulated by the collecting electrode 66. During later 10 seconds, only the ion generator 6c, 6d is switched ON and the plus charges of the plus ions generated by each ion generating unit 61 neutralize the minus ions accumulated by the collecting electrode 66. Therefore, the output voltage of the measuring unit 67 is decreased to the electrical potential of ground during the first half of 20 seconds, and increased toward the power voltage of the DC power (5V) during the last half of 20 seconds.

In the case that the ion presence is determined with the ion determination 1, it is determined that the ion is present when the difference between the maximum value and the minimum value of the output voltage during the period of ion determination 1 is larger than the predetermined threshold.

The drive signals input into the control inputs PC1-PC4 at each interval of the ion determination 2 are similar to those of ion determination 1, but the interval period (2 seconds) for switching ON/OFF of each drive signal is different from the interval period (20 seconds) of the ion determination 1.

In the case that the ion presence is determined with the ion determination 2, it is determined that the ion is present when the difference between the maximum value and the minimum value of the output voltage during the period of ion determination 2 is larger than the predetermined threshold.

Figure 10:
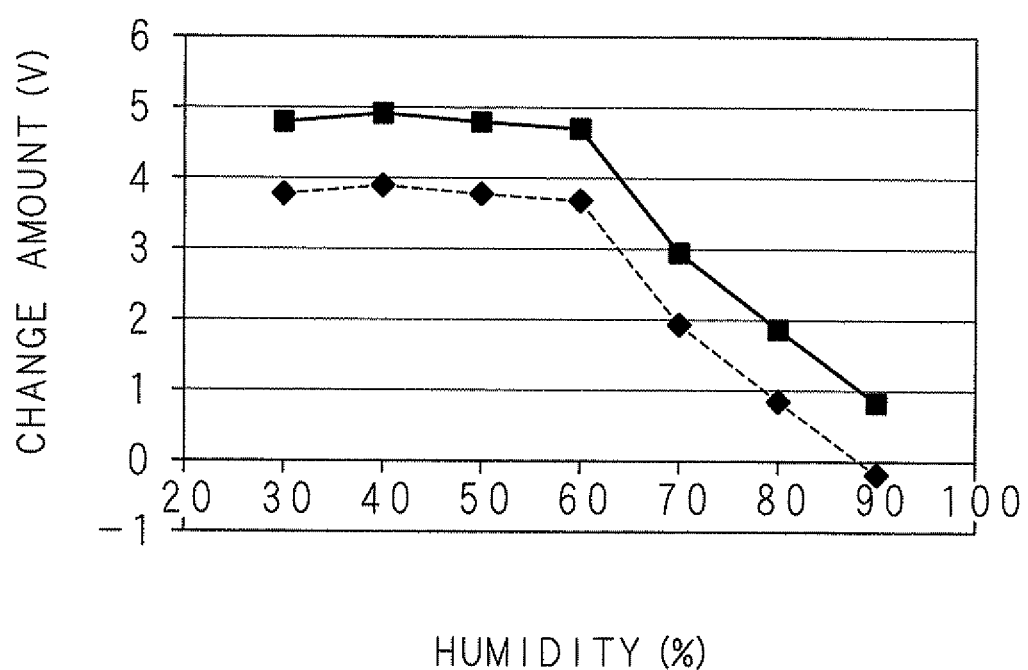
FIG. 10 is a graph that shows an example of a relationship between a change amount of output voltage of the measuring unit and the humidity.

FIG. 10 is a graph that shows an example of a relationship between a change amount of output voltage of the measuring unit 67 and the humidity. The horizontal axis represents the humidity (%) and the vertical axis represents the change amount (V) of the output voltage of the measuring unit 67 in the figure. In addition, the solid line represents the change amount of the output voltage of the measuring unit 67 and the broken line represents the thresholds utilized for the ion determination 1 and the ion determination 2.

In this figure, the change amount of the output voltage of the measuring unit 67 is approximately steady at 30-60% humidity (i.e., the ion amount measured by the measuring unit 67 is approximately steady). Thus, it is expected that the humidity has little effect on the measuring accuracy of the measuring unit 67. However, the change amount of the output voltage of the measuring unit 67 is decreased at over 60% humidity. Especially, under the high humidity condition where the humidity is 90% or more, the change amount of the output voltage of the measuring unit 67 is less than 1V. Thus, it is difficult to measure.

Hence, the ion generating apparatus according to the embodiment detects the humidity in the duct 5 by the humidity detecting unit 80, and leave the measuring unit 67 undone the ion measurement when the detected humidity is equal to or more than 90%. Therefore, it is possible to prevent the false determination of ion presence under the high humidity condition where the measurement is difficult.

The ion generating apparatus according to the embodiment performs the measurement of ion when the humidity detected by the humidity detecting unit 80 is less than 90%. For the determination of ion presence, the threshold compared to the change amount of the output voltage of the measuring unit 67 is set in accordance with the humidity. The threshold is set to be an approximately equal value for the humidity not more than 60% that have little effect, and set to be smaller value for higher humidity over 60%.

The ROM 82 of the ion generating apparatus previously stores a table representing the relationship between the humidity and the threshold. The CPU 81 refers the table stored by the ROM 82, and obtains the threshold for the ion presence determination based on the humidity detected by the humidity detecting unit 80. The optimal value of the threshold with respect to the humidity is different in accordance with the positional relationship between the ion generators 6a-6d and the collecting electrode 66. Thus, a designer or the like previously determines the optimal value during the design stage of the ion generating apparatus or the like, and then the relationship between the humidity and the threshold is stored as the table by ROM 82 during the design stage of the ion generating apparatus or the like.

Because the humidity detecting unit 80 is arranged in the duct 5 and the threshold for the ion presence determination is set in accordance with the humidity detected by the humidity detecting unit 80 as described above, it is possible to perform the accurate determination of ion presence in consideration of the humidity effect on the measuring unit 67. Although the example shown in FIG. 10 utilizes the threshold which is 1V smaller than the change amount of the output voltage of the measuring unit 67 (i.e., it is determined that the ion is not present when the change amount of the output voltage of the measuring unit 67 becomes lesser than 1V), the present invention is not limited to the example. For example, the threshold may be smaller by 0.5V or 1.5V. In addition, the example of FIG. 10 sets the threshold for every 10% humidity. However, the present invention is not limited to the example. The threshold may be set for every 5% or 2% humidity, based on the required accuracy for the ion presence determination.

It will be explained below with a flowchart about the operation of the ion generating apparatus described above.

Figure 11:
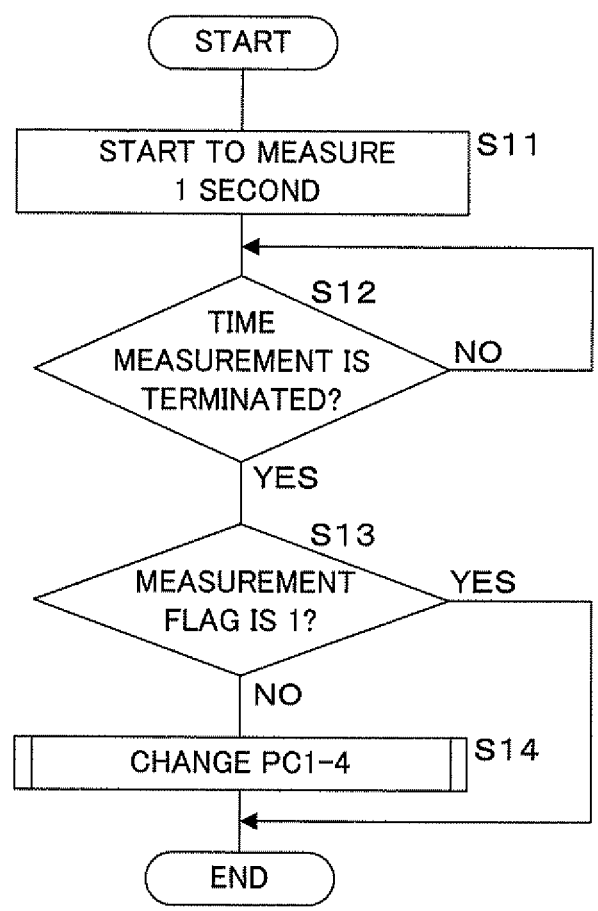
FIG. 11 is a flow chart that shows a procedure of a CPU driving the ion generator in the normal operable condition.
Figure 12:
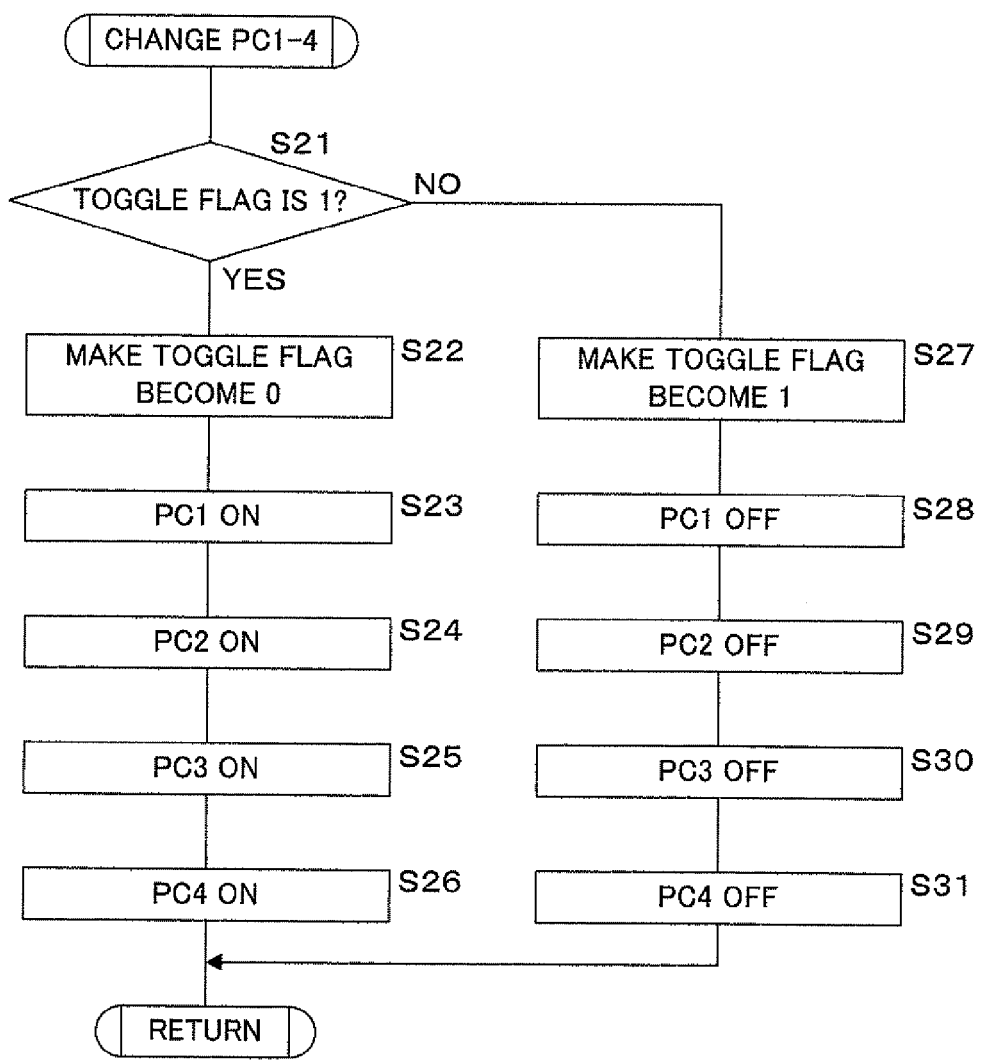
FIG. 12 is a flow chart that shows a procedure of the CPU for a subroutine for changing control inputs.

FIG. 11 is a flow chart that shows a procedure of the CPU 81 driving the ion generators 6a, 6b, 6c, 6d in the normal operable condition. FIG. 12 is a flow chart that shows a procedure of the CPU 81 for a subroutine changing the control inputs PC1-PC4. The procedures of FIG. 11 and FIG. 12 are based on the control program previously stored by the ROM 82. In addition, the procedure of FIG. 11 is repeated after the procedure is completed.

It should be noted that the RAM 83 stores the "measurement flag" representing the execution of measuring operation for determining the ion presence, and the "toggle flag" representing the phase of ON/OFF.

When the procedure of FIG. 11 is started, the CPU 81 makes the timer 84 start to measure 1 second (step S11). The measured time is not limited to 1 second. For example, the measured time may be 0.5 seconds, 1.5 seconds or the like. Then, the CPU 81 determines whether the timer 84 terminates the time measurement or not (step S12). When having determined that the timer 84 does not terminate the time measurement (step S12: NO), the CPU 81 waits until the timer 84 terminates the time measurement.

When having determined that the timer 84 terminates the time measurement (step S12: YES), the CPU 81 determines whether the "measurement flag" is set to be 1 or not (step S13). When having determined that the "measurement flag" is set to be 1 (step S13: YES), the CPU 81 terminates the procedure. Thus, the ion generators 6a, 6b, 6c, 6d are not switched ON/OFF in the procedure, during the execution of the ion presence determination. When having determined that the "measurement flag" is not set to be 1 (step S13: NO), the CPU 81 reads and executes the subroutine for changing the control inputs PC1-4 (step S14), and terminates the procedure.

When the subroutine for changing the control inputs PC1-4 shown in FIG. 12 is read out, the CPU 81 determines whether the "toggle flag" is set to be 1 or not (step S21). When having determined that the "toggle flag" is set to be 1 (step S21: YES), the CPU 81 clear the value of the "toggle flag" to be 0 (step S22), and makes the control input PC1 of the ion generator driving circuit 91 become ON through the output interface 88 (step S23). Similarly, the CPU 81 makes the control input PC2 become ON (step S24), the control input PC3 become OFF (step S25), further the control input PC4 become OFF (step S26) and then terminates the procedure.

When having determined at the step S21 that the "toggle flag" is not set to be 1 (step S21: NO), the CPU 81 sets the "toggle flag" to be 1 (step S27), and makes the control input PC1 of the ion generator driving circuit 91 become OFF through the output interface 88 (step S28). Similarly, the CPU 81 makes the control input PC2 become OFF (step S29), the control input PC3 become ON (step S30), further the control input PC4 become ON (step S31) and then terminates the procedure.

As described above, the CPU 81 changes ON/OFF of the control inputs PC1, PC2 and PC3, PC4 of the ion generator driving circuit 91.

Figure 13:
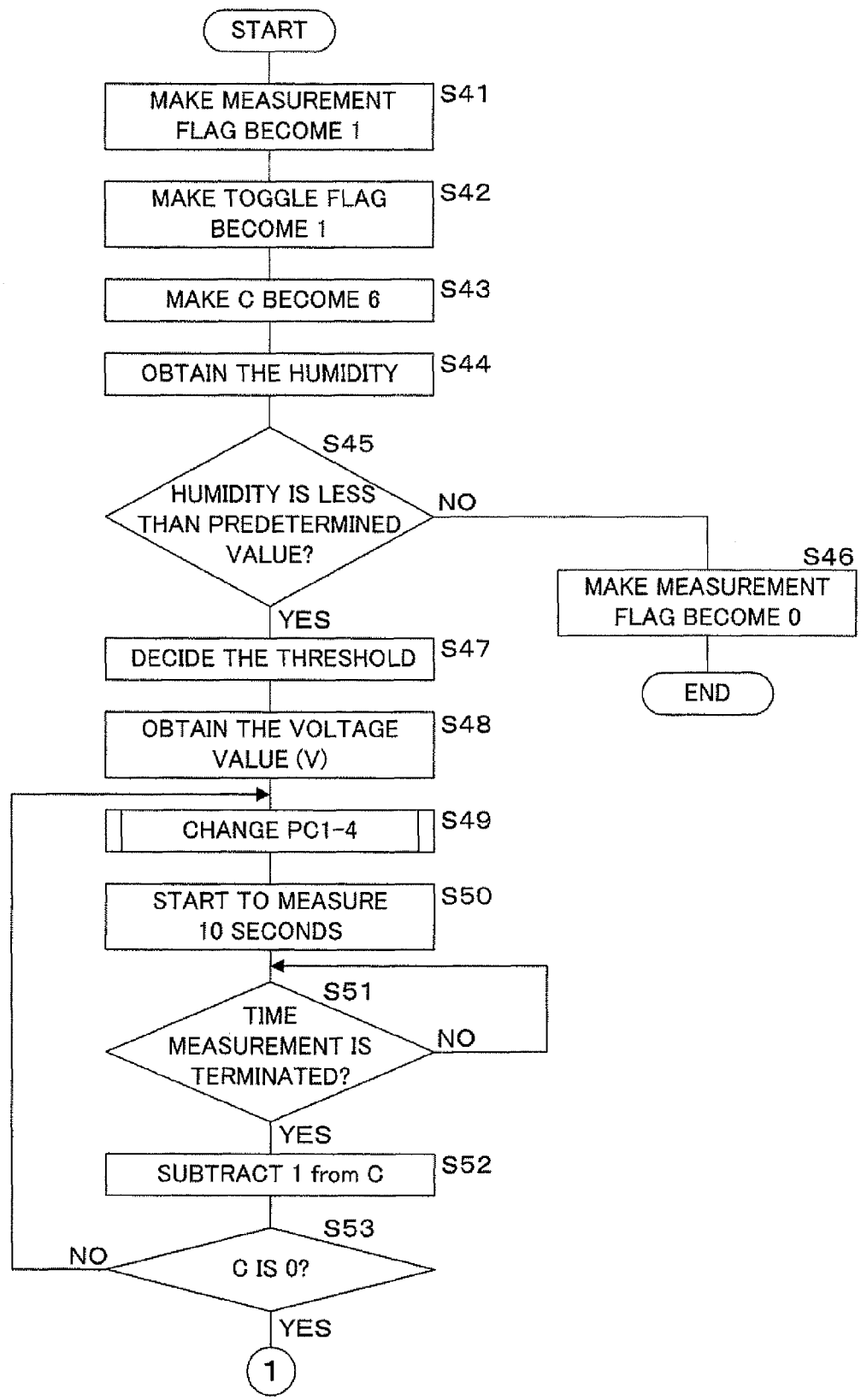
FIG. 13 is a flow chart that shows a procedure of the CPU warning in accordance with the determination result of the ion presence.
Figure 14:
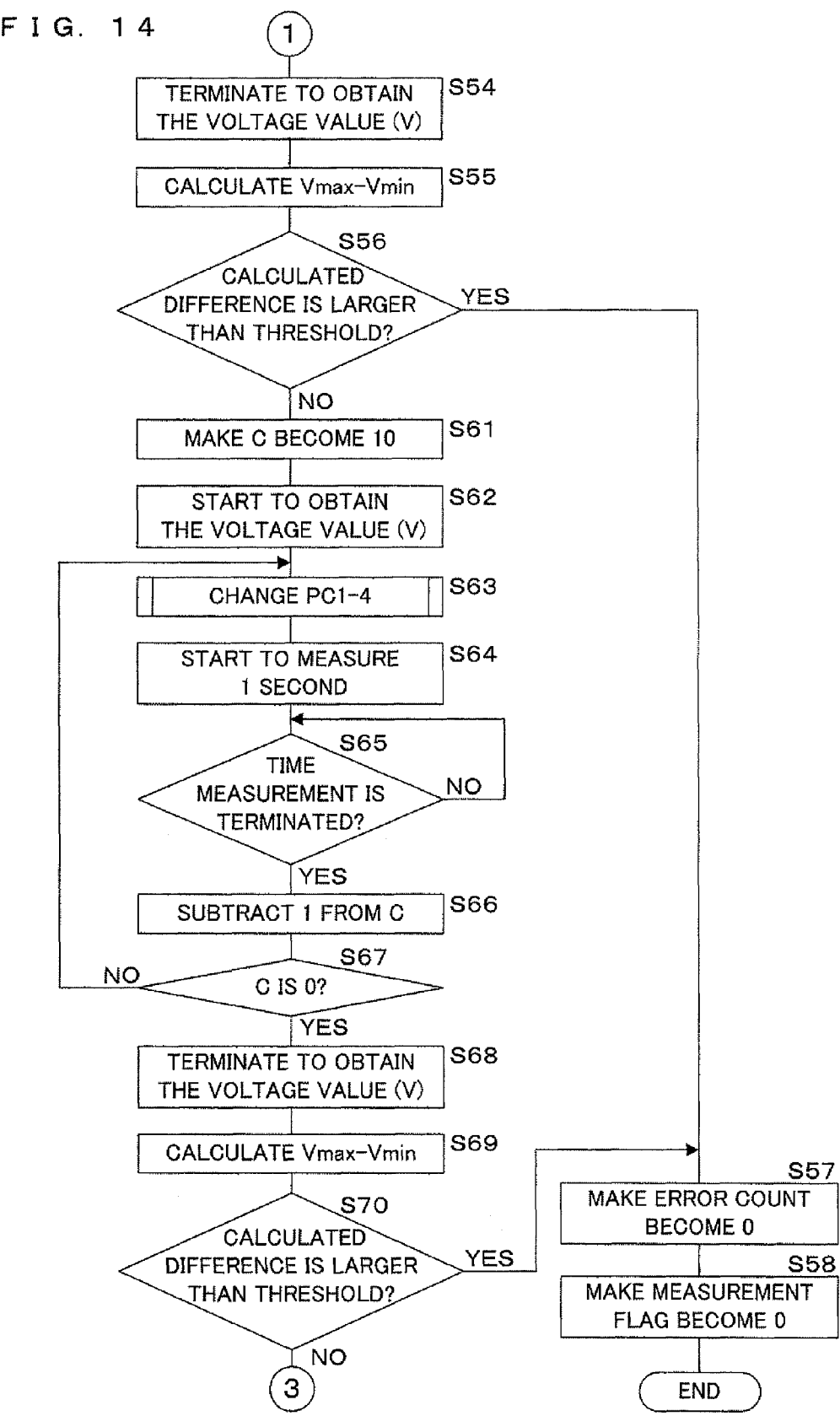
FIG. 14 is a flow chart that shows a procedure of the CPU warning in accordance with the determination result of the ion presence.
Figure 15:
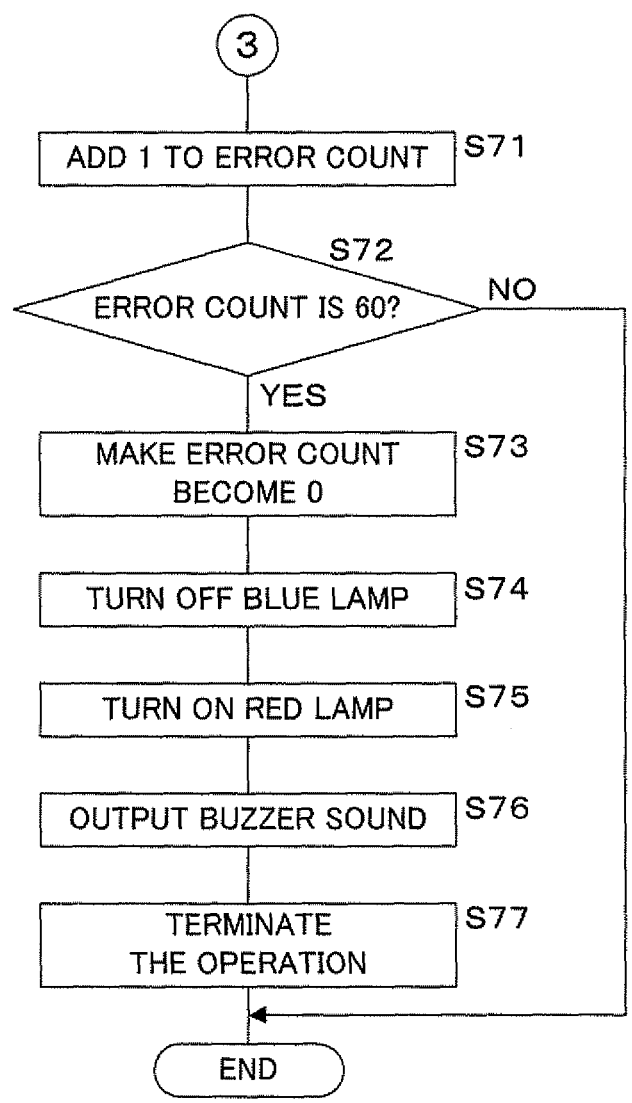
FIG. 15 is a flow chart that shows a procedure of the CPU warning in accordance with the determination result of the ion presence.

FIG. 13-FIG. 15 are flow charts that show a procedure of the CPU 81 warning in accordance with the determination result of the ion presence. The following procedure is based on the control program previously stored by the ROM 82, started 30 seconds later of the initialization process performed by the CPU 81, and then repeated every 3 hours. It should be noted that the repeat interval is not limited to 3 hours.

A "loop count (C)" and an "error count" are variable values stored by the RAM 83. The value 0 is written into the "error count" during the initialization process performed by the CPU 81.

When the procedure of FIG. 13-14 is started, the CPU 81 sets the value of the "measurement flag" to be 1 as the initial setting (step S41), sets the value of the "toggle flag" to be 1 (step S42), and substitutes 6 to the "loop count (C)" that stores the change number of the control inputs PC1-4 with the ion determination 1 (step S43). Then, the CPU 81 obtains the humidity detected by the humidity detecting unit 80 (step S44), and determines whether the detected humidity is less than a predetermined humidity (e.g., 90%) or not (step S45). When the detected humidity is equal to or more than the predetermined humidity (S45: NO), the CPU 81 clears the value of "measurement flag" to be 0 8step S46), and terminates the procedure without determining the ion presence.

When the humidity detected by the humidity detecting unit 80 is lower than the predetermined humidity (S45: YES), the CPU 81 refers to the table that represents the relationship of the humidity and the threshold and is stored by the ROM 82, and decides the threshold utilized for the ion presence determination (step S47). Then, the CPU 81 starts to obtain the voltage value (V) of the output voltage of the measuring unit 67 through the A/D converting circuit 89 (step S48). The obtained voltage value (V) is sequentially stored by a resistor of the CPU 81 or the RAM 83.

Then, the CPU 81 reads out and executes the subroutine (see FIG. 12) for changing the control inputs PC1-4 (step S49), and starts the timer 84 to measure 10 seconds (step S50). Then, the CPU 81 determines whether the timer 84 terminates the measurement or not (step S51). When having determined that the timer 84 does not terminate the measurement (step S51: NO), the CPU 81 waits until the timer 84 terminates the measurement.

When having determined that the timer 84 terminates the measurement (step S51: YES), the CPU 81 subtracts 1 from the "loop count (C)" (step S52), and determines whether the "C" becomes 0 or not (step S53). When having determined that the "C" does not become 0 (step S53: NO), the CPU 81 returns the procedure to the step S49. Thus, the switch of the control inputs PC1-4 is repeated.

When having determined at the step S53 that the "C" becomes 0 (step S53: YES), the CPU 81 terminates to obtain the voltage value (V) of the output voltage of the measuring unit 67 (step S54). Then, the CPU 81 calculates the difference (change amount of the voltage value) between the maximum value and the minimum value for the voltage value (V) stored in the register or the RAM 83 (step S55), and determines whether the calculated difference is larger than the threshold decided at the step S47 or not (step S56). When having determined that the difference is larger than the threshold (step S56: YES), i.e., when having determined that the ion is present, the CPU 81 clears the value of the "error count" to be 0 (step S57), further clears the value of the "measurement flag" to be 0 (step S58) for showing that the ion presence determination is terminated, and then terminates the procedure. Then, the determination history showing that the ion is not present is cleared.

When having determined that the difference is smaller than the threshold (step S56: NO), i.e., when having determined that the ion is not present, the CPU 81 substitutes 10 from the "loop count (C)" storing the change number of the control inputs PC1-4 with the ion determination 2 (step S61). Then, the CPU 81 starts to obtain the voltage value (V) of the output voltage of the measuring unit 67 through the A/D converting circuit 89 (step S62). Then, the obtained voltage value (V) is sequentially stored in the register of the CPU 81 or the RAM 83.

Then, the CPU 81 reads out and executes the subroutine for changing the control inputs PC1-4 (step S63), and makes the timer 84 start 1 second (step S64). Then, the CPU 81 determines whether the timer 84 terminates the measurement or not (step S65). When having determined that the timer 84 does not terminate the measurement (step S65: NO), the CPU 81 waits until the timer 84 terminates the measurement.

When having determined that the timer 84 terminates the measurement (step S65: YES), the CPU 81 subtracts 1 from the "loop count (C)" (step S66), and determines whether the value of "C" becomes 0 or not (step S67). When having determined that the value of "C" does not become 0 (step S67: NO), the CPU 81 returns the procedure to the step S63.

When having determined that the value of "C" becomes 0 (step S67: YES), the CPU 81 terminates to obtain the voltage value (V) of the output voltage of the measuring unit 67 (step S68). Then, the CPU 81 calculates the difference between the maximum value and minimum value of the voltage values (V) stored by the register or the RAM 83 (step S69), and determines whether the calculated difference (change amount) is larger than the threshold decided at the step S47 (step S70). When having determined that the difference is larger than the threshold (step S70: YES), i.e., when having determined that the ion is present, the CPU 81 returns the procedure to the step S57.

When having determined that the difference is smaller than the threshold (step S70: NO), i.e., when having determined that the ion is not present not only with the ion determination 1 but also with the ion determination 2, the CPU 81 adds 1 to the "error count" (step S71) and determines whether the value of the "error count" becomes 60 or not (step S72). When having determined that the value of the "error count" does not become 60 (step S72: NO), the CPU 81 terminates the procedure.

When having determined that the value of the "error count" becomes 60 (step S72: YES), i.e., when having determined that the ion is not present, the CPU 81 clears the value of the "error count" to be 0 (step S73), turns off a blue lamp of the display 86 for notifying that the ion is not present (step S74) and turns on a red lamp notifying the warning (step S75). Furthermore, the CPU 81 outputs the buzzer sound of the controller 85 in order to notify the warning by sound (step S76), performs required processing for terminating the operation (step S77), and terminates the procedure.

It should be noted that the determination number of the "error count" is not limited to 60, and may be an arbitrary value.

As described above, the embodiment determines that the ion is present (or not present), when the ion generator mainly generating pus ions and the ion generator mainly generating minus ions for the collecting electrode are turned on at the different timing with each other and then the difference of the output voltage of the measuring unit becomes larger (or smaller) than the threshold. In addition, the humidity detecting unit 80 is arranged in the duct 5, the threshold for the determination is set in accordance with the humidity detected by the humidity detecting unit, and the ion presence determination is not performed with the humidity more than the predetermined value, e.g., 90%.

Thus, it is possible to prevent the false determination of the ion presence, even under the high humidity condition where it is difficult to determine the ion presence. Therefore, it is possible to implement the accurate determination of the ion presence without the humidity effect.

In addition, ion generators whose alignment directions of the plus and minus ion generating units are the same are arranged without the overlay of them in the alignment direction, and the alignment directions are substantially perpendicular to the direction of air flowing near the ion generating units, respectively. Thus, the collecting electrode can collect ions generated by the plus ion generating unit of one ion generator and ions generated by the minus ion generating unit of another ion generator, respectively.

Hence, the difference in the output voltages of the measuring unit when each ion generator turns on at the different timing becomes larger than the change amount of the output voltage obtained when one ion generator is turned on/off. Therefore, it is easy to perform the ion presence determination.

In addition, ion generators are arranged to be opposed to each other in the alignment direction of the ion generating units, and the opening side of each ion generating unit is opposed to one direction perpendicular to the arrangement direction.

Thus, the distance between the collecting electrode and the arranged ion generator can be a minimum. Therefore, it is possible to accurately perform the ion presence determination because the difference of the output voltage of the measuring unit substantially becomes the local maximum when the each ion generator is turned on at the different timing. Furthermore, it is possible to efficiently flow the ions with the air flow in the air duct, as the ions are generated into the air duct by each ion generating unit.

In addition, the ion generator mainly generating pus ions and the ion generator mainly generating minus ions are alternately switched ON at 20 second interval (every 10 seconds) with respect to the collecting electrode, in order to perform the ion presence determination.

Thus, it is configured to make no overlap of ON timing of the ion generators. It is possible to accurately perform the ion presence determination, because the difference in the output voltages of the measuring unit when each ion generator is switched ON at the different timing substantially becomes the local maximum. Furthermore, it is possible to reduce the possibility of the false determination, due to the repeat of the same processing, that the ion is not present, because the determination is performed cyclically.

In addition, when it is determined with the ion determination 1 having 20 second interval that the ion is not present, the ion generator mainly generating minus ions with respect to the collecting electrode is switched ON at 2 second interval and then the ion presence determination is performed, again.

Thus, the ion presence determination is based on the change amount of the output voltage of the measuring unit when one ion generator is switched ON, and utilizes the drastic change of the output voltage when the ion is changed from plus to minus. Therefore, it is possible to perform the ion presence determination without the failure, even when the output voltage of the measuring unit once changed is reversely changed during the period that the ion generator is ON, for example, when the humidity of air being the object for the ion presence determination becomes extremely higher.

In addition, when it is sequentially determined 60 times that the ion is not present, the warning is output to the users with the LED of the display and the buzzer of the controller.

Therefore, it is possible to urge the cleaning of the ion generating unit or the exchange of the ion generator because the information representing the decrease of ion generating amount is notified to the users.

In the embodiment, it is illustrated to arrange the humidity detecting unit 80 on the front wall 5a of the duct 5. However, the present invention is not limited to the illustration. The arrangement position of the humidity detecting unit 80 is not limited to the position as shown in FIG. 1 and FIG. 2. For example, the humidity detecting unit 80 may be arranged inside of the casing 4 or outside of the housing 1. In addition, it is illustrated that the measurement of the measuring unit 67 and the ion presence determination are not performed when the humidity detected by the humidity detecting unit 80 is equal to or more than the predetermined humidity. However, the present invention is not limited to the illustration. It may be configured that the measurement of the measuring unit 67 is performed but that the error count is not increased at the time of determination representing no ion, even when the detected humidity is equal to or more than the predetermined humidity.

Although it is illustrated in the embodiment that the red lamp of the display 86 is turned on and buzzer sound is output for the warning, the present invention is not limited to the illustration. For example, it may be configured to include an electronic speech circuit and a speaker for outputting warning voice sound.

In addition, it is illustrated for the ion determination 1 that the predetermined threshold is compared with the difference in the output voltages of the measuring unit 67 immediately before the ion generators 6a, 6b and ion generators 6c, 6d are switched ON/OFF. However, the present invention is not limited to the illustration. For example, it may be configured to obtain the output voltage of the measuring unit every 1 second during the period that the ion generators 6a, 6b are switched ON for 10 seconds and switched OFF for 10 seconds, decide the minimum value and the maximum value, and compares the threshold with the difference between the decided maximum value and the decided minimum value.

In addition, it is illustrated that the collecting electrode 66 is pulled up to the DC 5V by the resistance and the minus ion is focused for performing the ion presence determination. However, the present invention is not limited to the illustration. For example, the collecting electrode 66 may be pulled down to the electrical potential of ground by the resistance, and then the plus ion may be focused for performing the ion presence determination.

As this invention may be embodied in several forms without departing from the spirit of essential characteristics thereof, the present embodiment is therefore illustrative and not restrictive, since the scope of the invention is defined by the appended claims rather than by the description preceding them, and all changes that fall within metes and bounds of the claims, or equivalence of such metes and bounds thereof are therefore intended to be embraced by the claims.

EXPLANATION OF ITEM NUMBERS 1 housing
2 motor
3 bladed wheel
4 casing
5 duct
6a, 6b, 6c, 6d ion generator
61, 62 ion generating unit
66 collecting electrode (a part of ion detector)
67 measuring unit (a part of ion detector)
80 humidity detecting unit (humidity detecting means)
81 CPU (determining means, threshold setting means)
82 ROM
83 RAM
84 timer
85 controller
86 display (warning means)
91 ion generator driving circuit (driving circuit)

The invention claimed is:
1. An ion generating apparatus, comprising:
plural ion generators that respectively generate either positive or negative ions;
a driving circuit that drives the plural ion generators to cyclically control ON and OFF operation of the plural ion generators;
a collecting unit that collects the ions generated by the plural ion generators;

a measuring unit that measures an electrical value of the collecting unit;
a humidity detector that detects humidity; and
a determining unit that performs a determination whether ions are present or not, wherein
the plural ion generators alternately become ON or OFF,
a timing used in making one of the plural ion generators become ON by the driving circuit is different from a timing used in making another of the plural ion generators become ON by the driving circuit,
when the driving circuit controls ON with periodically different timing of one of the plural ion generators and another of the plural ion generators that generates ions having different positive and negative properties from ions generated by the one of the plural ion generators, the determining unit determines that ions are present, when difference of measurements obtained by the measuring unit at a time immediately before the one of the plural ion generators is controlled ON and at a time immediately after the one of the plural ion generators is controlled ON is larger than a predetermined threshold,
the determining unit does not perform the determination, when the humidity detected by the humidity detector is larger than a predetermined humidity, and
the ion generating apparatus further comprising a threshold changing unit that changes the predetermined threshold based on the humidity detected by the humidity detector.

2. An ion generating apparatus according to claim 1, wherein
each of the plural ion generators generates the positive ions and the negative ions based on a cyclical control performed by the driving circuit.

3. An ion generating apparatus according to claim 2, further comprising:
a warning unit that provides a warning when the determining unit sequentially determines predetermined times that ions are not present.

4. An ion generating apparatus according to claim 1, wherein
the measuring unit measures the electrical value of the collecting unit during one cyclical period of the driving circuit, and
the determining unit utilizes a difference of a maximum of the electrical value and a minimum of the electrical value in said one cyclical period, to perform the determination.

5. An ion generating apparatus according to claim 4, wherein
the threshold changing unit changes the predetermined threshold into a smaller value when the humidity detected by the humidity detector is higher, and changes the predetermined threshold into a larger value when the humidity detected by the detector is lower.

6. An ion generating apparatus according to claim 5, further comprising:
a warning unit that provides a warning when the determining unit sequentially determines predetermined times that ions are not present.

7. An ion generating apparatus according to claim 4, further comprising:
a warning unit that provides a warning when the determining unit sequentially determines predetermined times that ions are not present.

8. An ion generating apparatus according to claim 1, wherein
the threshold changing unit changes the predetermined threshold into a smaller value when the humidity detected by the humidity detector is higher, and changes the predetermined threshold into a larger value when the humidity detected by the detector is lower.

9. An ion generating apparatus according to claim 1, further comprising:
a warning unit that provides a warning when the determining unit sequentially determines predetermined times that ions are not present.

10. A method for performing a determination of an ion presence generated by plural ion generators that respectively generate either positive or negative ions, comprising:
a step of cyclically repeating a control, by using a driving circuit, that makes the plural ion generators alternately become ON or OFF;
a step of collecting, by a collecting unit, ions generated by the plural ion generators;
a step of obtaining a difference of electrical values of the collecting unit;
a step of performing a determination whether ions are present or not;
a step of detecting humidity; and
a step of leaving the determination unperformed, when the detected humidity is more than a predetermined humidity, wherein
when the driving circuit controls ON with periodically different timing of one of the plural ion generators and another of the plural ion generators that generate ions having different positive and negative properties from ions generated by the one of the plural ion generators, it is determined that ions are present when the obtained difference at a time immediately before the one of the plural ion generators is controlled ON and at a time immediately after the one of the plural ion generators is controlled ON is more than a predetermined threshold; and
the method further includes a step of changing, by a threshold changing unit, the predetermined threshold based on the humidity detected by the humidity detector.

11. An ion generating apparatus, comprising:
plural ion generators configured to respectively generate either positive or negative ions;
a driving circuit configured to drive the plural ion generators to cyclically control ON and OFF operation of the plural ion generators;
a conductive ion collector configured to collect the ions generated by the plural ion generators;
a measuring circuit configured to measure an electrical value of the conductive ion collector;
a humidity detector configured to detect humidity; and
a determining processor configured and programmed to determine whether ions are present or not, wherein
the plural ion generators alternately become ON or OFF,
a timing used in making one of the plural ion generators become ON by the driving circuit is different from a timing used in making another of the plural ion generators become ON by the driving circuit,
when the driving circuit controls ON with periodically different timing of one of the plural ion generators and another of the plural ion generators that generates ions having different positive and negative properties from ions generated by the one of the plural ion generators, the determining processor determines that ions are present, when difference of measurements obtained by the measuring circuit at a time immediately before the one of the plural ion generators is controlled ON and at a time immediately after the one of the plural ion generators is controlled ON is larger than a predetermined threshold, the determining processor does not perform the determination, when the humidity detected by the humidity detector is larger than a predetermined humidity, and the humidity detector is configured to provide a detected humidity value to the determining processor and the determining processor is configured and programmed to change the predetermined threshold based on the detected humidity value that has been detected by the humidity detector.

12. An ion generating apparatus according to claim 11, wherein each of the plural ion generators generates the positive ions and the negative ions based on a cyclical control performed by the driving circuit.

13. An ion generating apparatus according to claim 12, further comprising:

at least one of a display and an audible alarm that provides a warning when the determining processor sequentially determines predetermined times that ions are not present.

14. An ion generating apparatus according to claim 11, wherein the measuring circuit is configured to measure the electrical value of the conductive ion collector during one cyclical period of the driving circuit, and the determining processor utilizes a difference of a maximum of the electrical value and a minimum of the electrical value in said one cyclical period, to perform the determination.

15. An ion generating apparatus according to claim 14, wherein the determining processor changes the predetermined threshold into a smaller value when the humidity detected by the humidity detector is higher, and changes the predetermined threshold into a larger value when the humidity detected by the detector is lower.

16. An ion generating apparatus according to claim 15, further comprising:

at least one of a display and an audible alarm that provides a warning when the determining processor sequentially determines predetermined times that ions are not present.

17. An ion generating apparatus according to claim 14, further comprising:

at least one of a display and an audible alarm that provides a warning when the determining processor sequentially determines predetermined times that ions are not present.

18. An ion generating apparatus according to claim 11, wherein the determining processor changes the predetermined threshold into a smaller value when the humidity detected by the humidity detector is higher, and changes the predetermined threshold into a larger value when the humidity detected by the detector is lower.

19. An ion generating apparatus according to claim 11, further comprising:

at least one of a display and an audible alarm that provides a warning when the determining processor sequentially determines predetermined times that ions are not present.

* * * * *